(12) United States Patent
Majima et al.

(10) Patent No.: US 11,103,131 B2
(45) Date of Patent: Aug. 31, 2021

(54) LAPAROSCOPIC DEVICE AND ENDOSCOPIC SYSTEM

(71) Applicant: Konica Minolta, Inc., Tokyo (JP)

(72) Inventors: Masanao Majima, Tokyo (JP);
Yasuyuki Natsuno, Tokyo (JP); Akira Kunimoto, Tokyo (JP); Katsumi Fujiwara, Tokyo (JP); Junichi Jono, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 496 days.

(21) Appl. No.: 15/300,188

(22) PCT Filed: Mar. 13, 2015

(86) PCT No.: PCT/JP2015/057555
§ 371 (c)(1),
(2) Date: Sep. 28, 2016

(87) PCT Pub. No.: WO2015/146652
PCT Pub. Date: Oct. 1, 2015

(65) Prior Publication Data
US 2017/0143200 A1    May 25, 2017

(30) Foreign Application Priority Data
Mar. 28, 2014 (JP) ............................. JP2014-068461
Mar. 28, 2014 (JP) ............................. JP2014-068491

(51) Int. Cl.
*A61B 1/313* (2006.01)
*A61B 1/00* (2006.01)
(Continued)

(52) U.S. Cl.
CPC ............ *A61B 1/313* (2013.01); *A61B 1/0008* (2013.01); *A61B 1/00071* (2013.01);
(Continued)

(58) Field of Classification Search
CPC ... A61B 1/313; A61B 1/00071; A61B 1/0008; A61B 1/00154; A61B 1/015; A61B 1/05;
(Continued)

(56) References Cited

U.S. PATENT DOCUMENTS 5,127,393 A * 7/1992 McFarlin ........... A61B 1/00154
600/114
2010/0010298 A1* 1/2010 Bakos .................... A61B 1/015
600/106
(Continued)

FOREIGN PATENT DOCUMENTS

JP    H11-119037 A    4/1999
JP    2008-018007 A    1/2008

OTHER PUBLICATIONS

Schrader, Malcolm E., "Wettability of Clean Metal Surfaces", Aug. 1984, Journal of Colloid and Interface Science, vol. 100, Issue 2, pp. 372-380 (Year: 1984).*

(Continued)

*Primary Examiner* — Ryan N Henderson
*Assistant Examiner* — Pamela F Wu
(74) *Attorney, Agent, or Firm* — Osha Bergman Watanabe & Burton LLP

(57) ABSTRACT

A laparoscopic device includes a flexible insertion part including an imaging optical system and an illumination optical system that are covered with an exterior tube; and an operational part connected to a base end of the insertion part. The insertion part is inserted into a peritoneal dialysis catheter for observation of an abdominal cavity, and the insertion part includes a distal extended part that is extendable from the peritoneal dialysis catheter in the abdominal cavity during use and formed in a shape with a curved part having a cumulative central angle between 180° and 360°.

11 Claims, 32 Drawing Sheets

(51) Int. Cl.
*A61B 1/015* (2006.01)
*A61B 1/05* (2006.01)
*A61B 1/06* (2006.01)
*A61M 1/28* (2006.01)
*G02B 23/24* (2006.01)
*A61B 90/00* (2016.01)

(52) U.S. Cl.
CPC .......... *A61B 1/00154* (2013.01); *A61B 1/015* (2013.01); *A61B 1/05* (2013.01); *A61B 1/0676* (2013.01); *A61M 1/285* (2013.01); *G02B 23/2476* (2013.01); *A61B 2090/3925* (2016.02); *A61B 2090/3966* (2016.02); *G02B 23/243* (2013.01); *G02B 23/2461* (2013.01)

(58) Field of Classification Search
CPC .......... A61B 1/0676; A61B 2090/3925; A61B 2090/3966; A61B 1/3132; A61B 1/3135; A61B 1/3137; A61B 1/317; A61B 1/00073; A61B 1/00075; A61B 1/00078; A61B 1/005; A61B 1/0051; A61B 1/01; A61B 1/012; A61B 1/0125; A61B 1/018; A61B 1/12; A61B 1/125–128; A61B 1/00131; A61B 1/00133; A61B 1/00135; A61B 1/00142; A61B 1/00147; A61B 1/00151; A61B 1/00087; A61B 1/00064; A61B 1/00066; A61M 1/285

USPC ........ 600/104, 109, 112–114, 121–125, 128, 600/130, 136, 139–142, 144, 146, 600/153–180; 604/164.01–164.13, 604/167.01–167.06
See application file for complete search history.

(56) References Cited

U.S. PATENT DOCUMENTS

| | | | |
|---|---|---|---|
| 2012/0310147 A1* | 12/2012 | Poll .................... | A61B 17/3417 604/24 |
| 2013/0304034 A1* | 11/2013 | Cabiri ............... | A61M 25/0138 604/528 |
| 2015/0245848 A1* | 9/2015 | Shimon ............. | A61M 25/0668 606/190 |
| 2016/0051280 A1* | 2/2016 | Dejima ............. | A61B 1/00087 600/114 |

OTHER PUBLICATIONS

International Search Report issued in PCT/JP2015/057555 dated Jun. 9, 2015 (2 pages).
Written Opinion of the International Searching Authority issued in PCT/JP2015/057555 dated Jun. 9, 2015 (4 pages).
English translation of the International Preliminary Report on Patentability and Written Opinion issued in corresponding International Application No. PCT/JP2015/057555 dated Oct. 13, 2016 (7 pages).

* cited by examiner

LAPAROSCOPIC DEVICE AND ENDOSCOPIC SYSTEM

TECHNICAL FIELD

The present invention relates to a laparoscopic device and an endoscopic system.

BACKGROUND ART

To detect an onset of peritonitis or encapsulating peritoneal sclerosis (EPS) in an early stage, which may occur due to peritoneal dialysis, it is effective to periodically observe the condition in the abdominal cavity by means of an endoscope.

However, an abdominal incision is required for introducing a typical endoscope into the abdominal cavity, which brings pain and strain to a patient.

In this regard, an effective method that brings less pain to a patient is to introduce an endoscope into the abdominal cavity by utilizing a peritoneal dialysis catheter that is in use for peritoneal dialysis.

When an endoscope is inserted through a peritoneal dialysis catheter, it is normally difficult to guide the endoscope to a position for observing the great omentum and the small intestine in order to check peritonitis and EPS since the opening of the peritoneal dialysis catheter in the abdominal cavity is placed near the Douglas' pouch.

Patent Document 1 describes a fiber scope that includes an image transmitting medium constituted by a multi-core image fiber of integrated optical fibers. The image transmitting medium has a bent part so that a front end face is oriented sideways relative to the image transmitting medium. The bent part is produced by plastically deforming the image transmitting medium so that the bent part has no residual strain. The curvature radius of the bent part is equal to or greater than the radius of the image transmitting medium.

The invention of Patent Document 2 is directed to observing the abdominal cavity by using a peritoneal dialysis catheter that has a slit formed in the side face for communicating the outside with the inside. An endoscope is inserted into the peritoneal dialysis catheter, and the front end of the endoscope is extended from the slit.

PRIOR ART DOCUMENTS

Patent Documents

Patent Document 1: JP H11-119037A
Patent Document 2: JP 2008-18007A

SUMMARY (A) In the invention described in Patent Document 1, the bent part is formed in the fiber scope for the purpose of suitably setting the view direction. Even with such conventional techniques using a bent part, it is difficult, after inserting the endoscope through a peritoneal dialysis catheter, to guide the front end of an endoscope to a location opposed to the great omentum and the small intestine and to place it in an angle in which the great omentum and the small intestine are sufficiently included in the field of view in order to check peritonitis and EPS.

One or more embodiments of the present invention provide a laparoscopic device that can be inserted through a peritoneal dialysis catheter and extended in the abdominal cavity from the peritoneal dialysis catheter, and the front end can be guided to a location opposed to the great omentum and the small intestine and placed in an angle in which the great omentum and the small intestine are sufficiently included in the field of view.

(B) In the methods such as described in Patent Document 2, which involve providing a slit that is formed in the side face of a catheter for a communication between the outside and the inside and inserting an endoscope into the abdominal cavity through the slit, an improper exchange of dialysis fluid may occur due to a leak of the dialysis fluid through the slit. Further, since it is difficult to insert the endoscope into the slit, the endoscope may be stuck in the slit, and it may become unable to remove the endoscope.

In the case where an endoscope is extended from the terminal opening of an indwelling catheter with the terminal end placed deep in the body cavity, such as a peritoneal dialysis catheter, only the deep part of the body cavity can be observed.

It is difficult to guide the front end of the endoscope to a required observation point away from the terminal opening of the indwelling catheter only by pushing, pulling and rotating the endoscope inserted in the indwelling catheter. Further, such movement may damage a living tissue in the body cavity or displace the indwelling catheter from the retained position.

One or more embodiments of present invention provide an endoscopic system that can guide the front end of an endoscope to a required observation point through an indwelling catheter.

A laparoscopic device according to one or more embodiments includes:

a flexible insertion part comprising an imaging optical system and an illumination optical system which are covered with an exterior tube; and an operational part connected to a base end of the insertion part, wherein the insertion part is inserted into a peritoneal dialysis catheter for observation of an abdominal cavity, and wherein the insertion part comprises a distal extended part which is extendable from the peritoneal dialysis catheter in the abdominal cavity during use and which is formed in a shape with a curved part having a cumulative central angle of greater than 180° to 360° or less.

According to one or more embodiments, the curved part of the distal extended part comprises a first curved part and a second curved part located in a written order from an front end, the distal extended part comprises a straight part with a straight center axis between the first curved part and the second curved part, and the first curved part has a central angle of from 30° to 150°, and the second curved part has a central angle of from 90° to 180°.

According to one or more embodiments, the insertion part is formed in a loop shape in which a front end of the distal extended part crosses a part continuing from a proximal end of the distal extended part of the insertion part.

A laparoscopic device according to one or more embodiments includes:

a flexible insertion part comprising an imaging optical system and an illumination optical system which are covered with an exterior tube; and an operational part connected to a base end of the insertion part, wherein the insertion part is inserted into a peritoneal dialysis catheter for observation of an abdominal cavity, wherein the insertion part comprises a distal extended part which is extendable from the peritoneal dialysis catheter in the abdominal cavity and which is formed in a shape with a curved part, wherein the curved part of the distal extended part comprises a first curved part and a second curved part in a written order from an front end, wherein the first curved part has a central angle of from 30° to 150°, and the second curved part has a central angle of from 90° to 180°, and wherein a plane including a curved center axis of the first curved part intersects with a plane including a curved center axis of the second curved part.

According to one or more embodiments, a marker which is detectable from outside by means of X-ray or ultrasound is provided in the insertion part along a center axis.

An endoscopic system according to one or more embodiments includes:

a flexible insertion part comprising an imaging optical system and an illumination optical system which are covered with an exterior tube;

an operational part connected to a base end of the insertion part; and a guide catheter in which the insertion part is inserted and which thereby guides the insertion part, wherein the guide catheter is configured to be inserted through an indwelling catheter and has a function of guiding the insertion part in a direction different from a guide direction by a terminal end of the indwelling catheter when the guide catheter is extended from a terminal opening of the indwelling catheter, in which the function is achieved by a curvature of a distal extended part of the guide catheter.

According to one or more embodiments, the curvature of the distal extended part of the guide catheter is due to an originally formed curved shape of the distal extended part or due to a bending mechanism that is operated during use for bending the distal extended part.

According to one or more embodiments, a front end of the insertion part has an originally formed curved shape or comprises a bending mechanism which is operated during use for bending the front end.

An endoscopic system according to one or more embodiments, further includes:

a fluid feeding means; and a joint wherein the joint comprises:

a first connector part configured to be connected to a proximal end of the indwelling catheter;

a second connector part connected to an output end of the fluid feeding means;

an insertion opening in which the guide catheter is inserted; and a channel which communicate the first connector part to the second connector part at one end and the insertion opening at the other end through a confluent part, wherein the joint is configured such that the guide catheter entering from the insertion opening to the channel can pass through the confluent part and the first connector part so as to enter the indwelling catheter connected to the first connector part, and wherein the joint is configured such that fluid fed from the fluid feeding means connected to the second connector part can pass through the confluent part and the first connector part so as to flow into the indwelling catheter connected to the first connector part.

According to one or more embodiments, the joint comprises a check valve between the insertion opening and the confluent part which prevents the fluid from leaking through the insertion opening.

According to one or more embodiments, the guide catheter comprises hydrophilic coating on an outer face thereof.

According to one or more embodiments, the guide catheter has a side hole.

According to one or more embodiments, the guide catheter comprises hydrophilic coating on an inner face thereof.

According to one or more embodiments, the guide catheter comprises hydrophilic coating on an outer face thereof.

According to one or more embodiments, the joint comprises a fixing mechanism which fixes the guide catheter to the joint, the guide catheter being inserted from the insertion opening.

According to one or more embodiments, a mark indicating an orientation of the curvature is provided in the guide catheter.

According to one or more embodiments, a mark indicating an inserted length is provided in the guide catheter.

According to one or more embodiments, a mark indicating an insertion length is provided in the insertion part.

According to one or more embodiments, the exterior tube comprises hydrophilic coating on an outer face thereof.

Effects of Invention

According to one or more embodiments, the insertion part can be inserted through a peritoneal dialysis catheter and extended from the peritoneal dialysis catheter in the abdominal cavity, and the front end thereof can be guided to a position opposed to the great omentum and the small intestine and placed at an angle in which the great omentum and the small intestine are sufficiently included in the field of view.

According to one or more embodiments, the insertion part of the endoscope is inserted in the guide catheter, and the guide catheter is inserted in the indwelling catheter, so that the insertion part of the endoscope is guided by the guide catheter in a direction different from the direction of the indwelling catheter. Therefore, it is possible to guide the front end of the endoscope that is inserted through the indwelling catheter to a desired observation point.

Further, the chance of damaging a living tissue in the body cavity or displacing the indwelling catheter from the retained position is reduced.

BRIEF DESCRIPTION OF DRAWINGS

FIG. 7B is in use.

DETAILED DESCRIPTION

Figure 1:
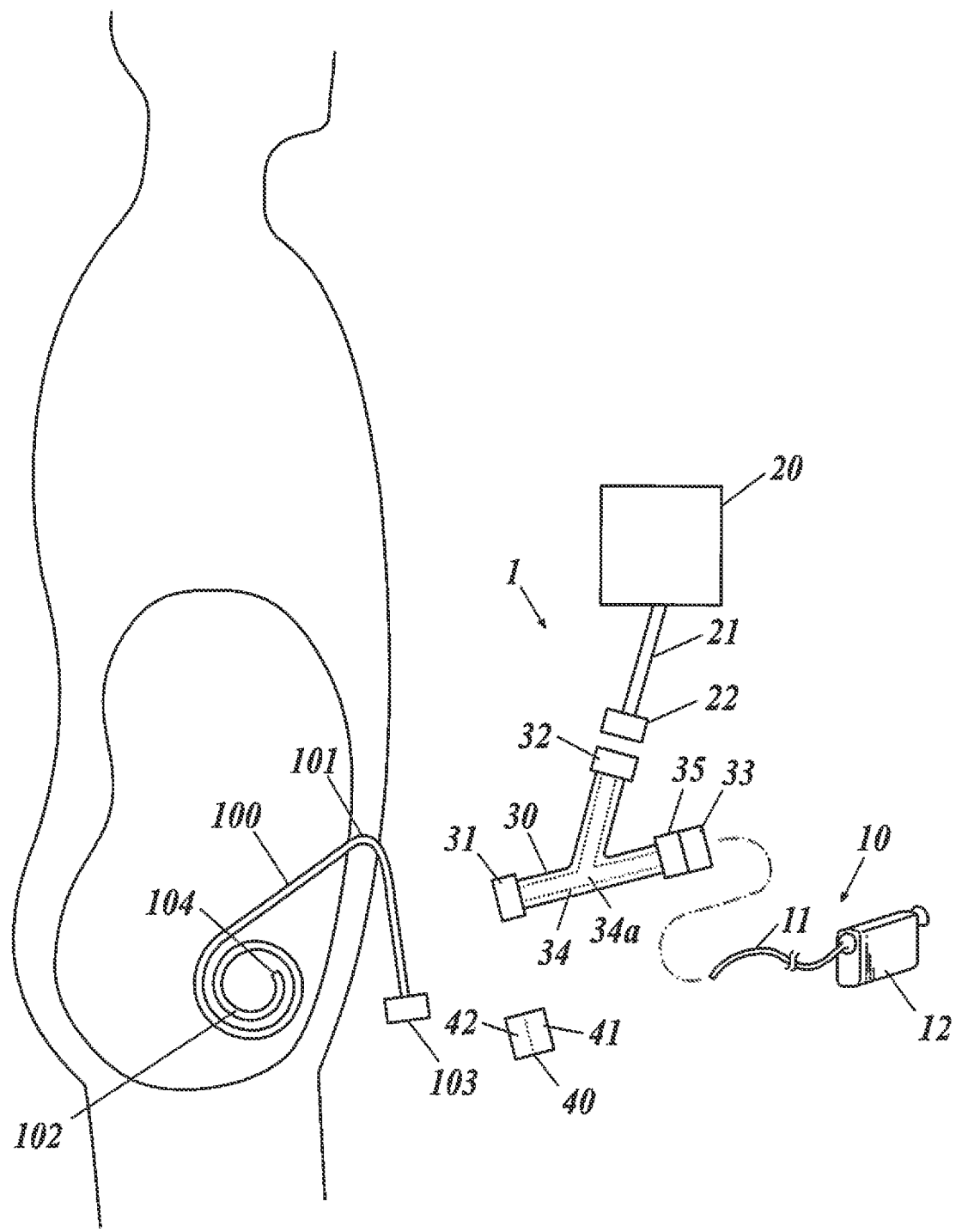
FIG. 1 is a schematic overview of an endoscopic system according to one or more embodiments of the present invention that illustrates the state in which the components are disconnected from each other.

Hereinafter, embodiments of the present invention will be described referring to the drawings. The following embodiments are merely some of the embodiments of the present invention, and the present invention is not limited thereto.

Embodiment A

FIG. 1 to FIG. 15B are referenced in this section.
Overview of System Configuration
First, the overview of a whole endoscopic system of one or more embodiments will be described.

Figure 2:
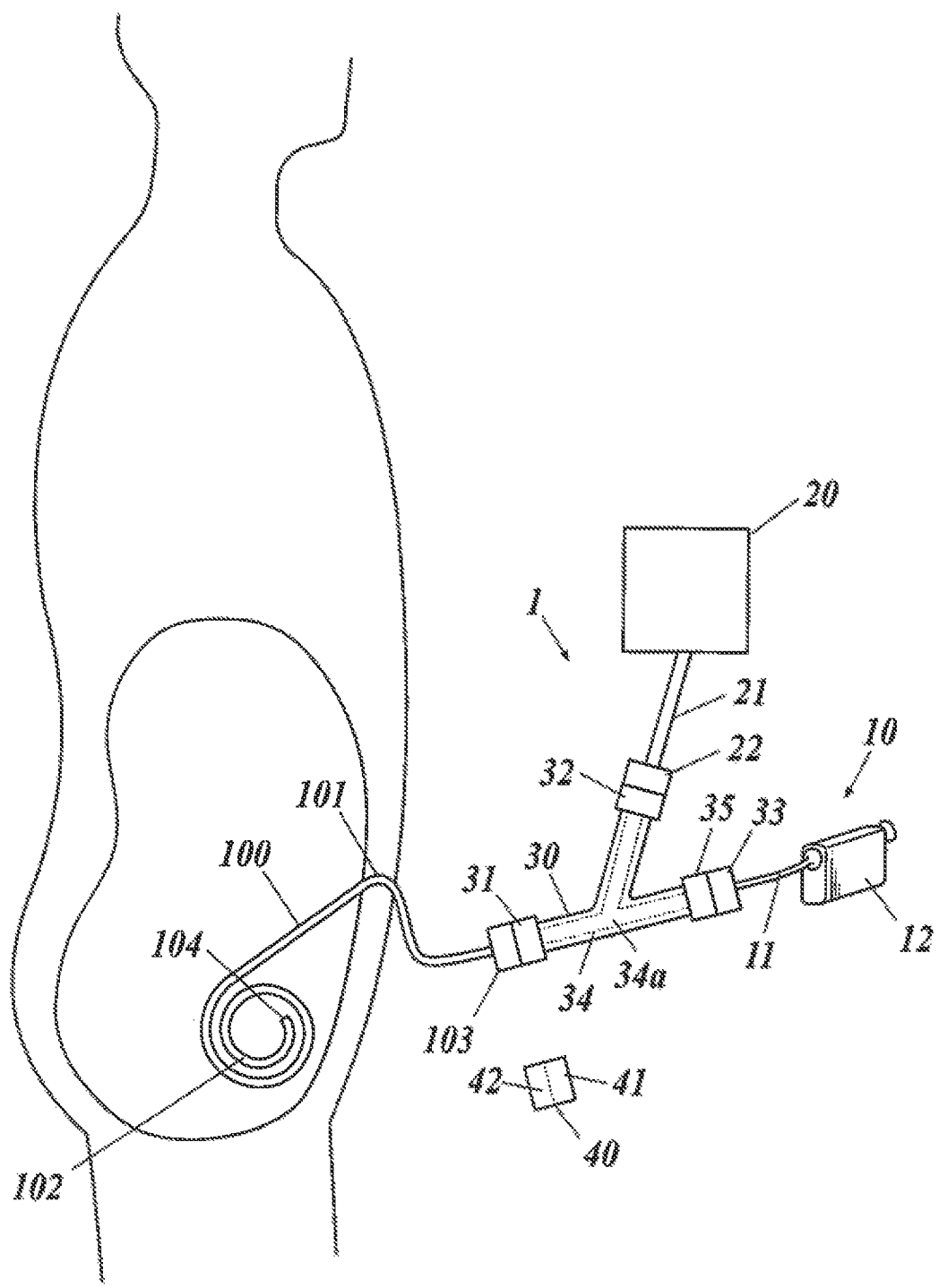
FIG. 2 is a schematic overview of the endoscopic system according to one or more embodiments of the present invention that illustrates the state in which the components are connected to each other.
Figure 3:
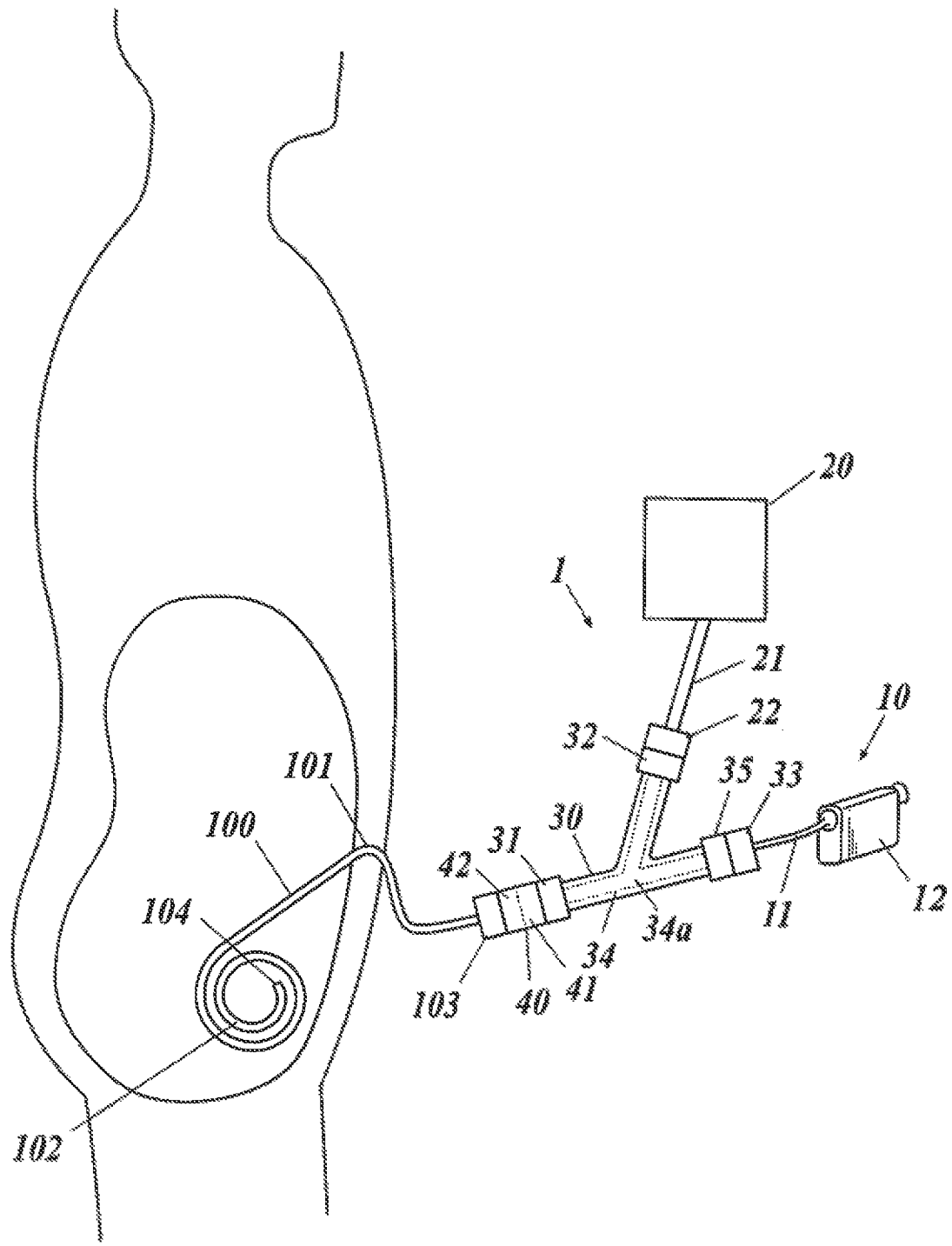
FIG. 3 is a schematic overview of the endoscopic system according to one or more embodiments of the present invention that illustrates the state in which the components including a conversion connector are connected to each other.

As illustrated in FIG. 1 to FIG. 3, the endoscopic system 1 of one or more embodiments include an endoscope 10, a fluid feeding means 20 and a joint 30. FIG. 1 illustrates the state in which the joint 30 and the other components are separated from each other. FIG. 2 illustrates the state in which the other components are connected with the joint 30, and the endoscope is inserted. FIG. 3 illustrates the state in which a conversion connector 40 is further connected.

The endoscope 10 is composed of an insertion part 11 and an operational part 12. The insertion part 11 is composed of an imaging optical system and an illumination optical system, which are covered with a protection tube.

For the imaging optical system, an imaging lens disposed at the front end of the insertion part 11 is used as well as an image fiber or an imaging element that transmits or takes an image formed by the imaging lens.

For the illumination optical system, a solid light emitting element that is disposed at the front end of the insertion part 11 or a light guide fiber that guides light from a light source disposed in the operational part 12 to the front end of the insertion part 11 is used.

The protection tube encloses the imaging optical system and the illumination optical system so as to constitute the exterior of the insertion part 11. The protection tube is made of a material with moderate flexibility and high surface slipperiness.

The operational part 12 is connected to the base end of the insertion part 11. In particular, the insertion part 11 and the operational part 12 are detachably connected with each other. With this configuration, it is possible to wash and sterilize only the insertion part 11 of the endoscope 10 by detaching the insertion part 11 from the operational part 12 or to use a disposable (non-reusable) insertion part 11 in order to maintain the quality and the hygiene.

That is, while catheters and endoscopes that are inserted into the body cavity are sterilized before use in order to prevent an infection, the component to be sterilized can be reduced to only the insertion part 11. The sterilization methods that can be used include EOG sterilization, autoclaving, γ-ray sterilization and the like.

Repetitive sterilization of the insertion part 11 may degrade the properties of the slip coating applied to the outer circumferential face of the protection tube. A connector part may be provided so that the insertion part 11 and the operational part 12 of the endoscope 10 are separable from each other, and the insertion part 11 is configured to be disposable after each use. This enables always supplying the insertion part 11 with good slipperiness, which facilitates an insertion into an indwelling catheter 100. In contrast to typical reusable endoscopes, being disposable eliminates the risk of infection cause by an insufficient wash or sterilization.

The operational part 12 is a handheld device that is held by an operator and is used for operations of the insertion part 11 such as back and forward movements and rotation around the axis. The operational part 12 also serves as a base end unit in which an optical or electrical component for lighting or imaging through the insertion part 11 is housed.

A bending operation mechanism may be further provided for a bending operation of the insertion part 11 by means of a wire coupled to the protection tube or the like. In this case, operation members such as a dial and a lever are disposed in the connector part at the base end of the insertion part 11 or in the operational part 12.

It is advantageous that the bent insertion part 11 has a curved shape. That is, the insertion part 11 originally has a curved shape in a no-load condition. The curved shape is such that the insertion part 11 curves in the vicinity of the front end within the range from 30° to 150°. By an operation on the operational part 12 of rotating the insertion part 11 around the axis, it is possible to turn the front end of the insertion part 11 toward the distal part of the indwelling catheter 100 in a curved part such as a bent part 101 and a spiral part 102 of the indwelling catheter 100. This facilitates bringing the insertion part 11 to the distal end 104 of the indwelling catheter 100. Further, by an operation on the operational part 12 of rotating the insertion part 11 around the axis, it is possible to change the view direction so as to observe a wider area. In this regard, it is desirable that the curvature of the insertion part 11 has an optimal specific shape according to the positional relationship between the distal end 104 of the indwelling catheter 100 and an observation subject and to the view angle of the imaging optical system of the insertion part 11. For example, in the case where the view angle of the imaging optical system is 60° in all directions and the curvature is set to 30°, the area ahead in the axial direction is always included in the field of view even when the insertion part 11 is rotated around the axis. Accordingly, the view of the distal part of the indwelling catheter, to which the insertion part 11 is inserted, is ensured during the operation.

It is advantageous that the insertion part 11 is configured such that the flexural rigidity decreases toward the front end. This facilitates inserting the insertion part 11 because the insertion part 11 can be easily forwarded even in a sharply bent part of the indwelling catheter 100 and the part with comparatively high rigidity near the base end facilitates transmitting a force for the insertion in the axial direction.

It is advantageous that the insertion part 11 includes a member that is disposed at a predetermined position and is detectable by means of X-ray or ultrasound. This is because when the insertion part 11 is inserted into the indwelling catheter 100, the insertion depth of the insertion part 11 can be checked, and the front end of the insertion part 11 can thereby be guided to a predetermined position at high positional accuracy.

For the fluid feeding means 20, an infusion bag, a syringe, an infusion pump, a syringe pump and the like for medical use are used. For example, an infusion bag is connected to the joint 30 via an infusion tube 21. When an infusion bag is used, an infusion pump can be used for mechanically feeding fluid. The infusion pump may be of roller type, finger type, volumetric type or the like. Instead of the infusion bag, a syringe is connected to the joint 30 directly or via the infusion tube 21. When the syringe is used, a syringe pump can be used for mechanically feeding fluid.

The joint 30 includes a first connector part 31, a second connector part 32, an insertion opening 33 and a communication channel 34.

The first connector part 31 is connected to the proximal end 103 of the indwelling catheter 100. The second connector part 32 is connected to the output end 22 of the fluid feeding means 20. The insertion opening 33 is used for inserting the insertion part 11.

The communication channel 34 is communicated to the first connector part 31, which is further communicated to the second connector part 32 and the insertion opening 33 via a confluence part 34*a*. The communication channel 34 is a channel member having a trifurcate structure in the confluence part 34*a*. The communication channel from the first connector part 31 to the insertion opening 33 is formed in a straight shape. This facilitates inserting the insertion part 11.

The joint 30 includes a check valve 35 between the insertion opening 33 and the confluence part 34*a* for preventing fluid from leaking though the insertion opening 33.

As illustrated in FIG. 2 and FIG. 3, the joint 30 with the above-described configuration allows the insertion part 11 to enter from the insertion opening 33 into the communication channel 34 to pass through the confluence part 34*a* and the first connector part 31 to enter the indwelling catheter 100 connected to the first connector part 31. Further, the joint 30 allows fluid fed from the fluid feeding means 20 connected to the second connector part 32 to pass through the confluence part 34*a* and the first connector part 31 to flow into the indwelling catheter 100 connected to the first connector part 31.

Accordingly, in the indwelling catheter 100 and the joint 30 connected to the indwelling catheter 100, the fluid from the fluid feeding means 20 can flow around the insertion part 11 in the direction toward the body cavity. The fluid reduces the friction between the insertion part 11 and the inner wall of the indwelling catheter 100. That is, the contact friction between the inner surface of the indwelling catheter 100 and the outer surface of the insertion part 11 can be reduced by feeding the fluid such as saline to the gap between the indwelling catheter 100 and the insertion part 11, and it is therefore possible to insert the insertion part 11 into the indwelling catheter 100 in a slippery condition. Further, the fluid makes a force of moving the insertion part 11 in the direction toward the body cavity, which facilitates inserting the insertion part 11 into the indwelling catheter 100.

For the fluid fed from the fluid feeding means 20, a biocompatible fluid is used. For example, when the indwelling catheter 100 is a peritoneal dialysis catheter, peritoneal dialysis solution can be used. A lubricant for a urethral catheter can also be used. Further, saline and the like can also be used. In addition to the biocompatibility, a fluid that improves the slipperiness between the insertion part 11 and the inner wall of the indwelling catheter 100 is selected.

The first connector part 31 is connected to the proximal end 103 of the indwelling catheter 100. There are the following two methods of adapting the first connector part 31 to a variety of indwelling catheters 100 with different sizes, shapes and attached connector parts of the proximal end 103.

One method involves providing many types of joints 30 with different structures of the first connector part 31 and selecting a joint 30 that includes a first connector part 31 connectable to the proximal end 103 of the indwelling catheter 100. However, the resource efficiency is low in this method.

The other method involves using a conversion connector 40 as illustrated in FIG. 3. The conversion connector 40 includes a third connector part 41 at one end 40*a* thereof that is connected to the first connector part 31 and also includes a fourth connector part 42 at the other end 40*b* thereof that is connectable to a counterpart structure different from the counterpart structure connectable to the first connector part 31. The adaptation can be achieved by providing various types of conversion connectors 40 with fourth connector parts 42 of different structures.

Configuration of Connector

Examples of connectors that can be used in the proximal end 103 of the indwelling catheter 100, the first connector part 31, the second connector part 32, the third connector part 41, the fourth connector part 42 and the output end 22 of the fluid feeding means 20 will be described.

Figure 4A:
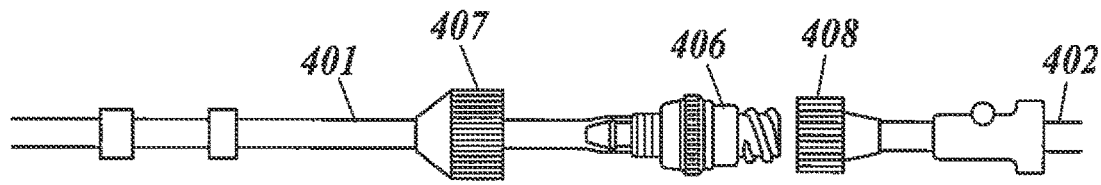
FIG. 4A is a type of tube connector.
Figure 4B:
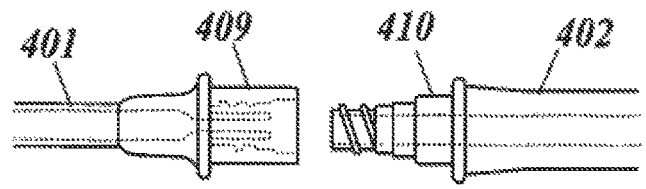
FIG. 4B is a type of tube connector.
Figure 4C:
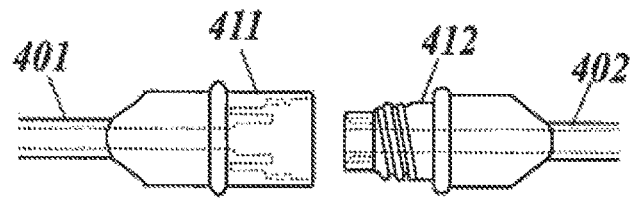
FIG. 4C is a type of tube connector.
Figure 4D:
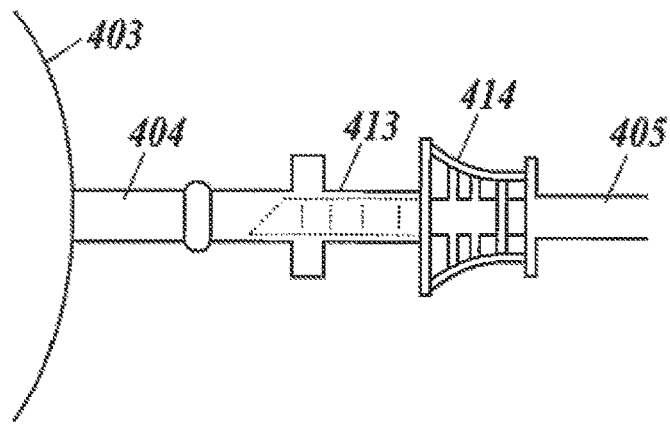
FIG. 4D is a type of tube connector.

Such connectors include a connector for peritoneal dialysis as illustrated in FIG. 4A, a luer connector as illustrated in FIG. 4B and a screw-in connector as illustrated in FIG. 4C. They are designed to connect a tube 401 and a tube 402 to each other. A spike connector as illustrated in FIG. 4D is designed to connect a tube 404 integrally formed with an infusion bag 403 to a tube 405.

The connector for peritoneal dialysis as illustrated in FIG. 4A includes a connector body part (male) 406, a locknut 407, a connector part (female) 408. The luer connector as illustrated in FIG. 4B includes a connector part (female) 409 and a connector part (male) 410. The screw-lock connector as illustrated in FIG. 4C includes a connector part (female) 411 and a connector part (male) 412. The spike connector as illustrated in FIG. 4D includes a connector part (female) 413 and a connector part (male) 414.

When the tube 401 in FIG. 4A is the indwelling catheter 100 and the connector part (female) 408 is employed as the first connector part 31, the indwelling catheter 100 is connectable to the joint 30. However, in this case, the first connector part 31 is connectable to neither connector part (female) 409 nor the connector part (female) 411. The conversion connector 40 is used. When the conversion connector 40 has the third connector part 41 that is formed in the shape of the connecting end of the connector part (male) 406 and the fourth connector part 42 that is formed in the shape of the connecting end of the connector part (male) 410, the first connector part 31 can be connected to the connector part (female) 409 via the conversion connector 40. Similarly, when the conversion connector 40 has the third connector part 41 that is formed in the shape of the connecting end of the connector part (male) 406 and the fourth connector part 42 that is formed in the shape of the connecting end of the connector part (male) 412, the first connector part 31 can be connected to the connector part (female) 411 via the conversion connector 40.

Figure 5:
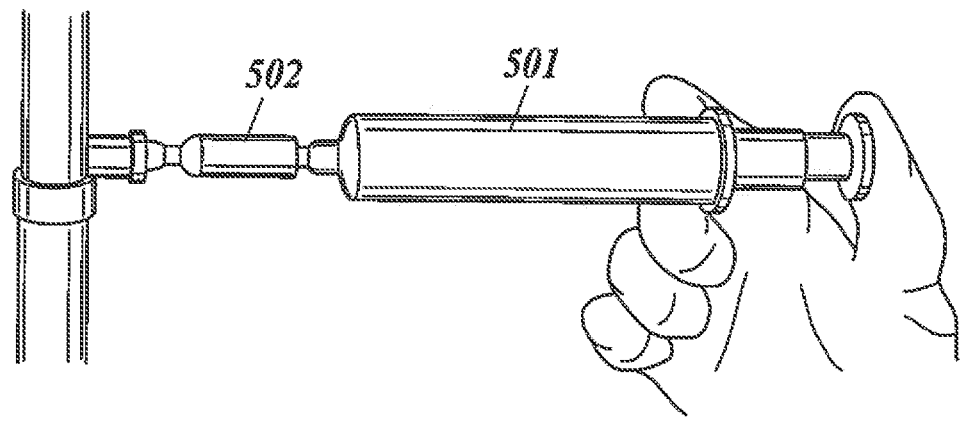
FIG. 5 illustrates a connector part provided in an infusion device and a syringe connected thereto.

Such conversion connectors can also be used between the fluid feeding means 20 and the second connector part 32. FIG. 5 illustrates an example of a connector part 502 that is connected to a syringe 501. When the connector part 502 is employed as the second connector part 32, the syringe 501 can be connected without an infusion tube.

Figure 6:
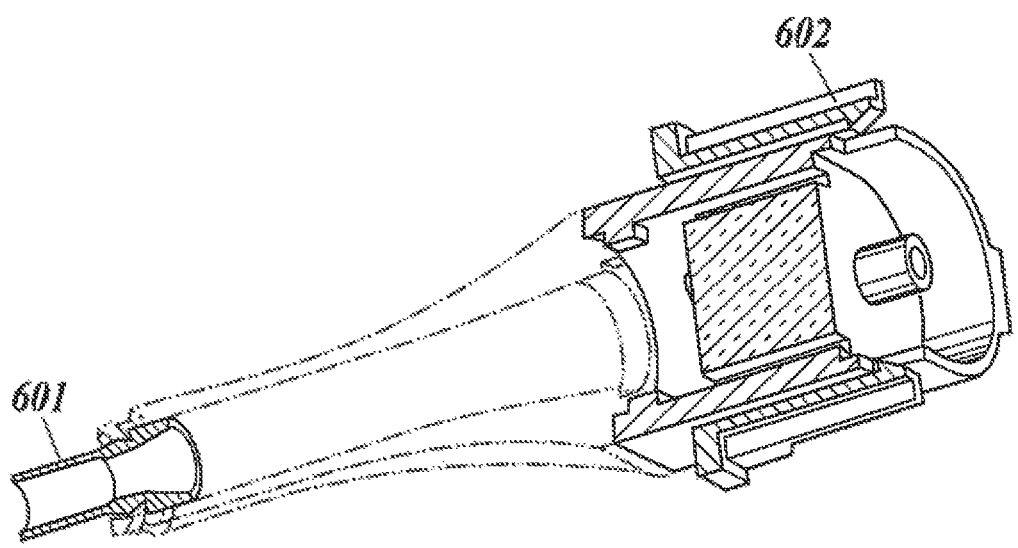
FIG. 6 is a cross sectional perspective view of snap-fit connector components.

Another proposal is a snap-fit connector as illustrated in FIG. 6. A tube 601 is connected to an end of the connector part in FIG. 6. The tube 601 corresponds to the indwelling catheter 100 or the infusion tube 21. The other end 602 is connected to a joint 30 in a snap-fit manner. The counterpart structure to receive the other end 602 in the snap-fit manner is formed in the first connector part 31 or the second connector part 32.

Configuration of Endoscope

Some configurations of the endoscope 10 will be described.

Configuration 1

Figure 7A:
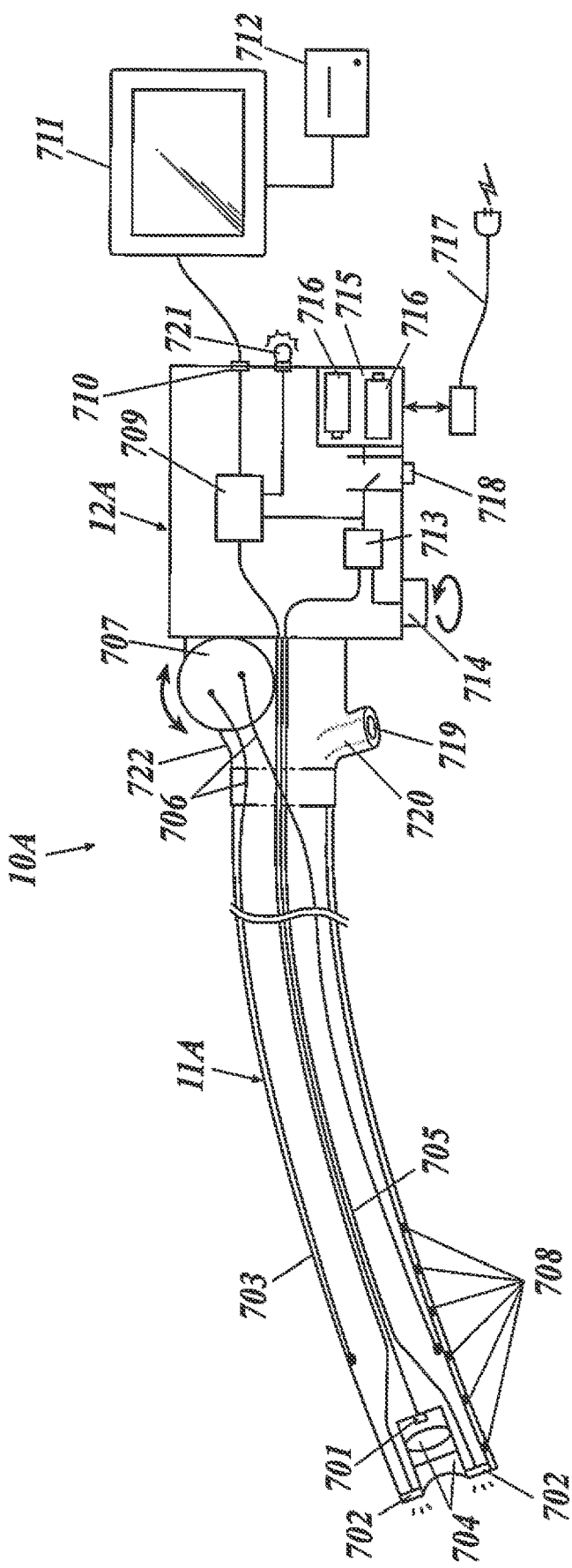
FIG. 7A is an overall configuration view of an endoscope that illustrates a configuration thereof.
Figure 7B:
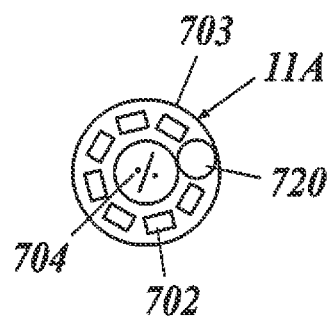
FIG. 7B illustrates the front end face of an insertion part of the endoscope of FIG. 7A.

FIG. 7A and FIG. 7B illustrate a configuration of the endoscope of one or more embodiments in which an imaging element 701 is used for the imaging optical system and a solid light emitting element 702 is used for the illumination optical system.

An endoscope 10A of FIG. 7A and FIG. 7B is composed of an insertion part 11A and an operational part 12A. The insertion part 11A is composed of an imaging optical system and an illumination optical system, which are covered with a protection tube 703. For the imaging optical system, an imaging lens 704 disposed at the front end of the insertion part 11A is used as well as an imaging element 701 that takes an image formed by the imaging lens 704 and an electric cable 705. For the imaging element 701, an electronic device that can perform photoelectric conversion such as a CCD (charge coupled device) or a CMOS imaging sensor is used. The electric cable 705 is provided to supply electric power to the imaging element 701 and the solid light emitting element 702 and to transmit a video signal taken by the imaging element 701. The solid light emitting element 702 is constituted by an LED (light emitting diode) in this configuration.

The protection tube 703 encloses the imaging optical system and the illumination optical system so as to constitute the exterior of the insertion part 11A. The protection tube 703 is made of a material with moderate flexibility and high surface slipperiness.

The operational part 12A is connected to the base end of the insertion part 11A. In particular, the insertion part 11A includes a connector part 722 at the base end so that it is detachable from the operational part 12A. The operational part 12A is a handheld device that can be held by an operator and is used for operations of the insertion part 11A such as backward and forward movements and rotations. The operational part 12A also serves as a base end unit that houses optical or electrical equipment for the lighting and imaging through the insertion part 11A.

In addition, a bending operation mechanism that bends the insertion part 11A by means of a wire 706 coupled to the protection tube 703 may be provided. In this case, an operation dial 707 is provided in the connector part 722 as the operation member thereof.

In the protection tube 703, a member (detection mark) 708 detectable by means of X-ray or ultrasound is embedded at a predetermined position.

The operational part 12A includes a video processor 709 that receives a video taken by the imaging element 701 through the electric cable 705 and outputs it to a video output terminal 710 after necessary image processing. The video is displayed on a video display monitor 711 connected to the video output terminal 710. The video output from the video output terminal 710 can be recorded on a recorder 712.

A light source driver 713 applies a drive current to the solid light emitting element 702 through the electric cable 705 so that the solid light emitting element 702 emits light. An operation member such as a light intensity adjustment knob 714 is provided in the operational part 12A so that the light intensity of the solid light emitting element 702 can be adjusted. The electrically driven part of the operational part 12A including the video processor 709 and a light source driver 713 is powered by a battery 716 loaded in a loading part 715 of the operational part 12A or by an AC power source connected through a power cable 717, and a power switch 718 is provided in the operational part 12A. The battery level of the battery 716 is indicated on an indicator 721.

Further, a channel opening 719 is formed in the connector part 722. The channel opening 719 is communicated with a channel 720.

Figure 8:
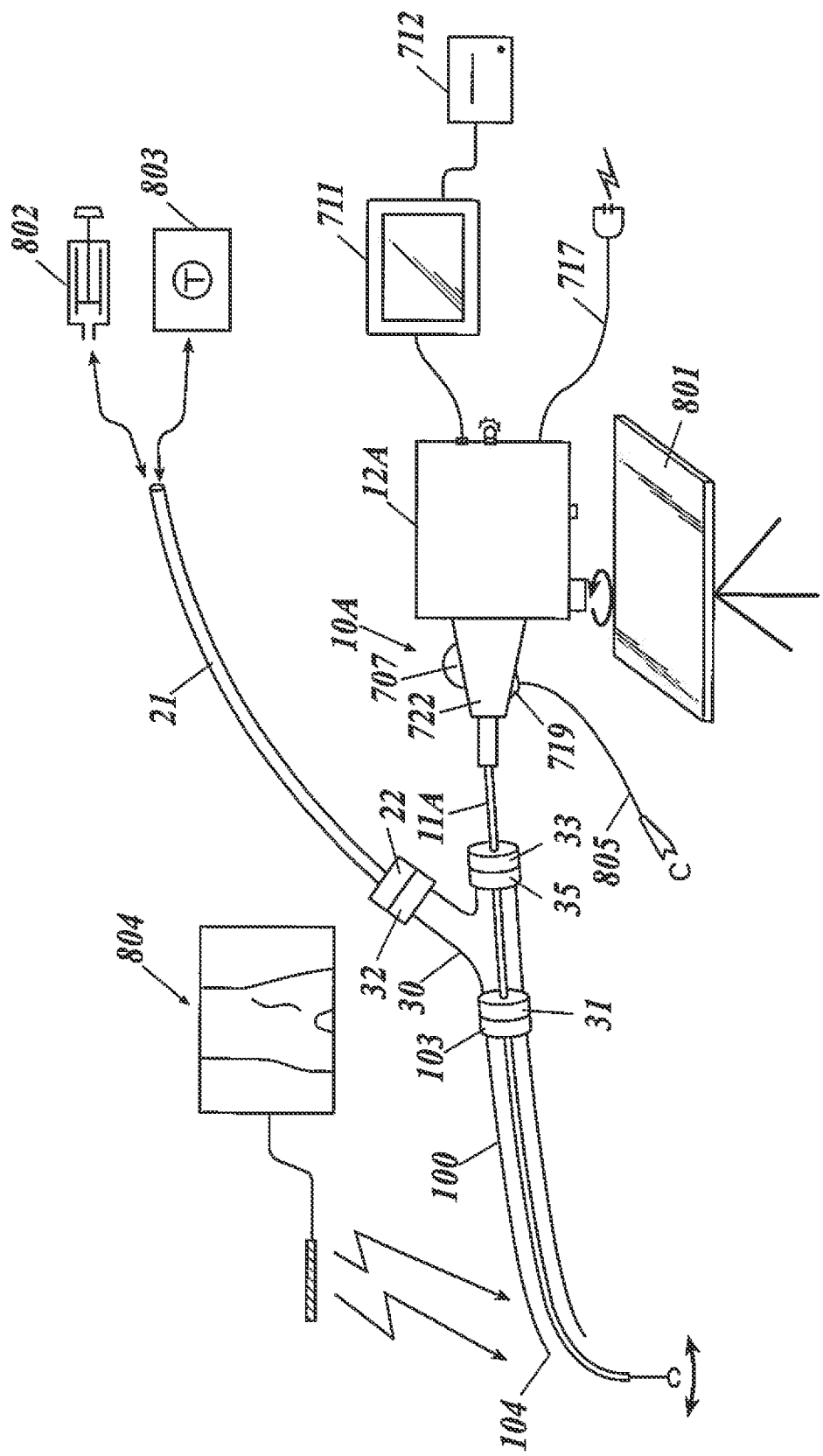
FIG. 8 is a schematic view of a scene where the endoscope of FIG. 7A

FIG. 8 illustrates a scene in use. For example, the video display monitor 711 and the recorder 712 are placed on a table 801, and the syringe 802 and the infusion pump 803 as the fluid feeding means 20 are further mounted according to need. The syringe 802 and the infusion pump 803 are connected to the joint 30 via the infusion tube 21. Further, the indwelling catheter 100 and the joint 30 are connected to each other. Thereafter, infusion is started, and the fluid is fed to the indwelling catheter 100. Simultaneously with or after starting the infusion, the insertion part 11A of the endoscope 10A is inserted through the insertion opening 33 of the joint 30. The insertion part 11A is inserted to a deep part while the location and position of the insertion part 11A is being monitored by detecting the member 708 by means of an X-ray or ultrasonic detector 804, in which the insertion part 11A is bent by using the operation dial 707 according to need. While the front end of the insertion part 11A is located inside the indwelling catheter 100, it is possible to observe the inside of the indwelling catheter 100, in which the insertion part 11A can be bent according to need. After the front end of the insertion part 11A gets out of the distal end 104 of the indwelling catheter 100, it is possible to observe the body cavity where the indwelling catheter 100 is placed, in which the insertion part 11A can be bent according to need. Further, a forceps 805 is inserted through the channel opening 719 and used according to need.

Configuration 2

Figure 9A:
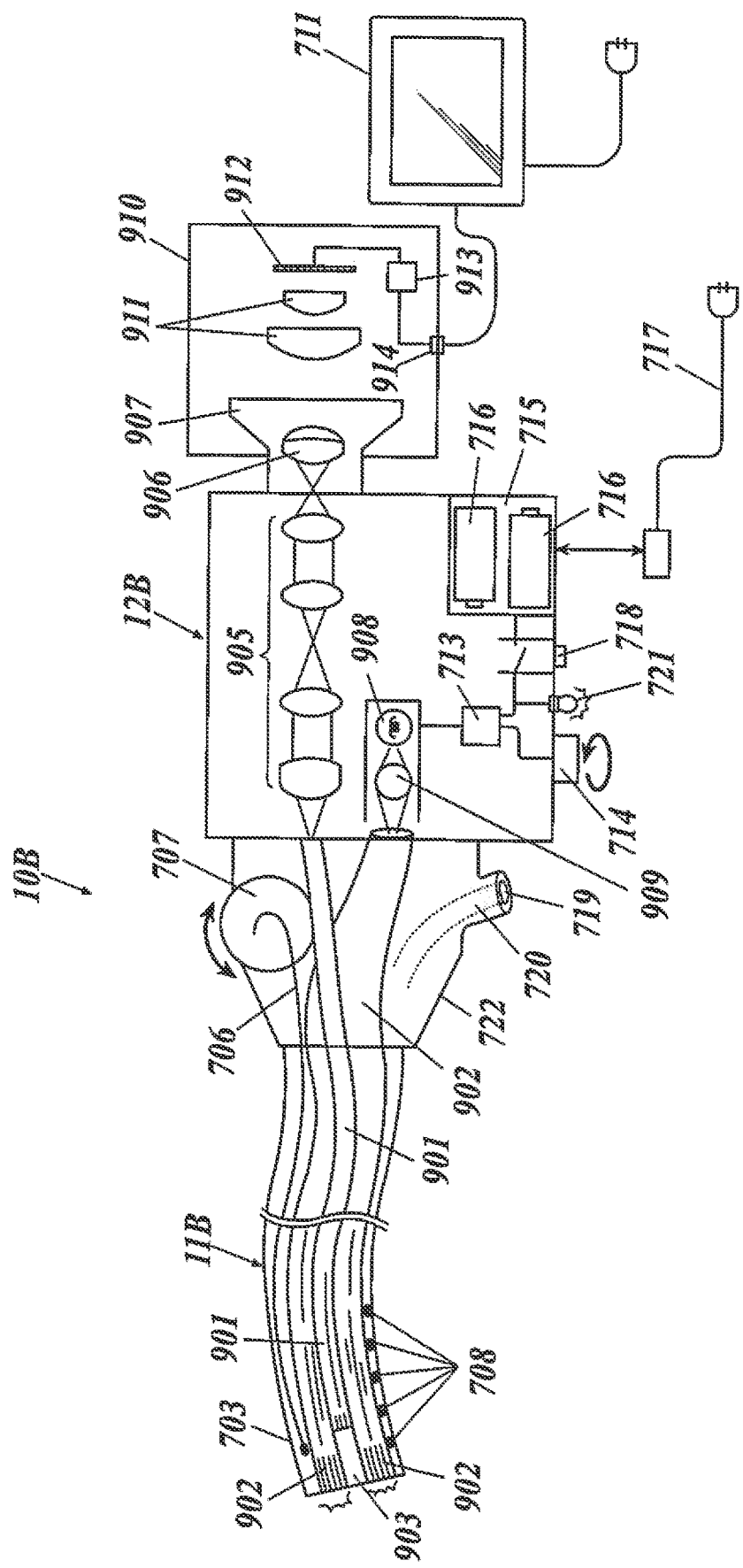
FIG. 9A is an overall configuration view of the endoscope that illustrates a configuration thereof.
Figure 9B:
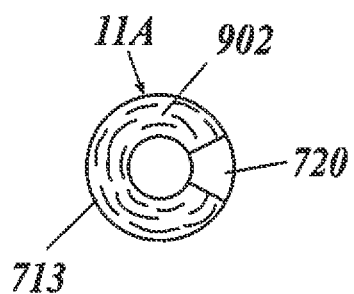
FIG. 9B illustrates the front end face of the insertion part of the endoscope of FIG. 9A.

FIG. 9A and FIG. 9B illustrates a configuration of the endoscope of one or more embodiments in which an image fiber 901 is used for the imaging optical system and a light guide fiber 902 is used for the illumination optical system.

An endoscope 10B of FIG. 9A and FIG. 9B is composed of an insertion part 11B and an operational part 12B. The same reference signs are denoted to the same components as those in FIG. 7A and FIG. 7B.

For the imaging optical system, an imaging lens (see FIG. 11A and FIG. 11B, reference sign 904) that is held by a lens frame 903 disposed at the front end of the insertion part 11B is used as well as the image fiber 901 that transmits an image formed by the imaging lens.

For the illumination optical system, the light guide fiber 902 is used.

The operational part 12B is connected to the base end of the insertion part 11B. The image fiber 901 is optically coupled to a relay optical system 905 disposed in the operational part 12B. The relay optical system 905 relays an image between the image fiber 901 and an eyepiece lens 906 so that the image transmitted from the image fiber 901 can be visually observed through an eyepiece unit 907.

In the operational part 12B, an illumination light source 908 is disposed. The light from the light source 908 enters the light guide fiber 902 through a coupling lens 909, is guided to the front end face of the insertion part 11B by the light guide fiber 902 and is casted to the observation object.

To output the image transmitted by the image fiber 901 to the video display monitor 711, a signal conversion adapter 910 is connected to the eyepiece unit 907. The signal conversion adapter 910, which includes an imaging lens 911, an imaging element 912, a video processor 913 and a video output terminal 914, outputs an image from the eyepiece lens 906 to the video output terminal 914 in the form of a video signal.

As described above, the image fiber 901 is used for the imaging optical system, which is constituted by thousands of optical fibers formed in a bundle. A GRIN lens is provided at the front end of the image fiber 901, which is fixed in close contact with the image fiber 901 and serves as the imaging lens.

For the illumination optical system, the light guide fiber 902 is provided to propagate light from the illumination light source to an observation object, which is constituted by hundreds of optical fibers formed in a bundle.

A flexible protection tube 703 is provided around the imaging optical system and the illumination optical system to avoid a contact between the living body and the optical components.

The optical fibers of the image fiber and the light guide fiber may be made of any material that has a transmittance and a color suitable for the usage, which can be selected from multi-component glass, silica glass and plastic (polymethylmethacrylate, polystyrene, styrene acrylonitrile, polyurethane and the like). The diameter, the NA, the number and the like of the optical fibers used may be suitably selected as long as they can be correctly assembled.

For the imaging optical system, a photo-electric element used in electronic endoscopes or the like may be used instead of the image fiber as described in Configuration 1. In this case, it is possible to obtain an image with a higher quality than in the case using the image fiber.

Configuration 3

Another possible configuration of one or more embodiments is a combination of the imaging optical system of Configuration 1 with the illumination optical system of Configuration 2.

Configuration 4

Another possible configuration of one or more embodiments is a combination of the imaging optical system of Configuration 2 with the illumination optical system of Configuration 1.

Configuration 5

Figure 10A:
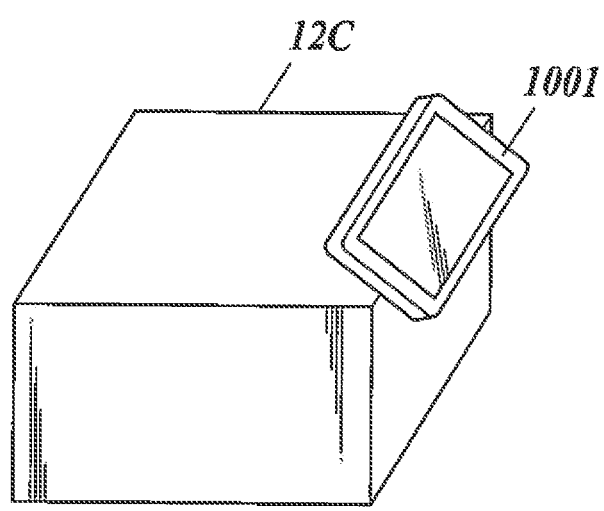
FIG. 10A is an outer appearance view of an operational part of the endoscope that illustrates a configuration thereof.
Figure 10B:
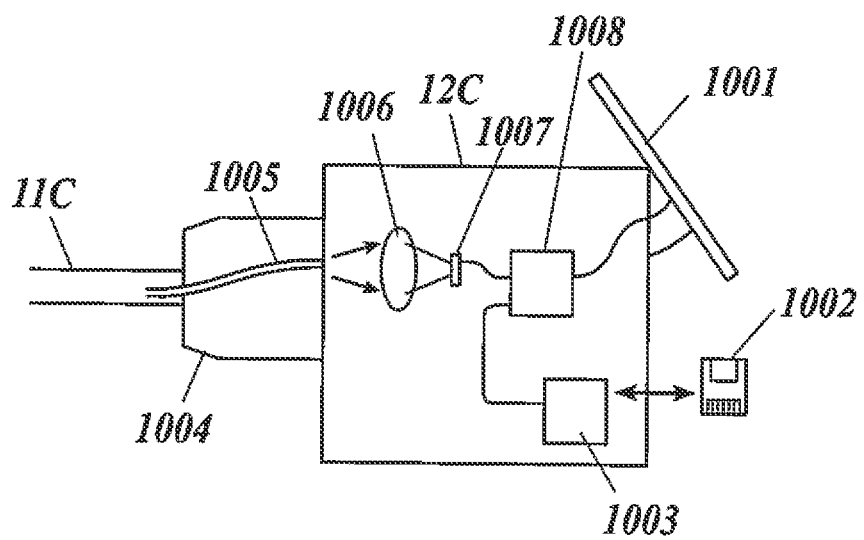
FIG. 10B is a configuration view of the operational part of the endoscope that illustrates a configuration thereof.

The operational part may have the function of the video display monitor and/or the recorder in FIG. 7A or the like. For example, a thin image display device 1001 is installed in an operational part 12C as illustrated in FIG. 10A. Further, a writer 1003 for a recording medium 1002 is installed in the operational part 12C as illustrated in FIG. 10B. In the illustrated example, an insertion part 11C of FIG. 10B includes a connector part 1004 and an image fiber 1005, and the operational part 12C includes an imaging lens 1006, an imaging element 1007 and a video processor 1008.

Configuration 6

Figure 10C:
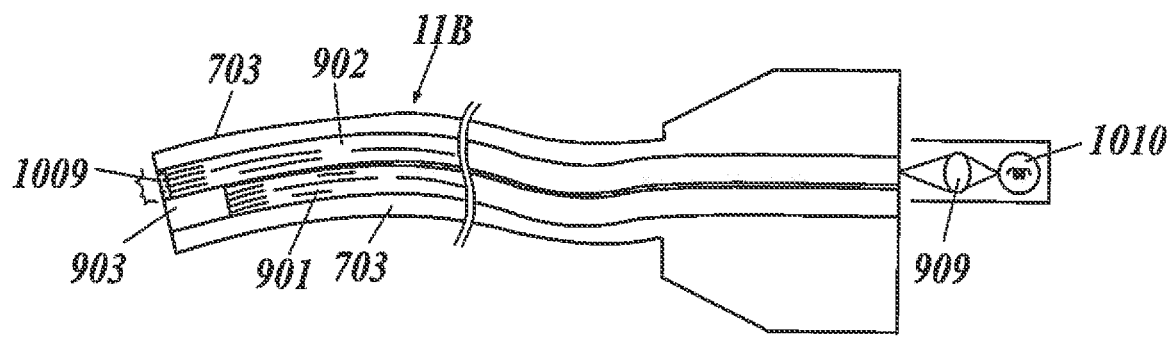
FIG. 10C is a vertical cross sectional view of the insertion part of the endoscope that illustrates a configuration thereof.

As illustrated in FIG. 10C, the illumination optical system may be configured such that a phosphor 1009, which is applied to the front end face of the light guide fiber 902 located at the front end face of the insertion part 11B, is irradiated with excitation light guided from a light source 1010 through the light guide fiber 902, the phosphor 1009 is thereby exited, and the light generated by the excitation is casted from the phosphor 1009 to an observation object as illumination light. That is, the phosphor 1009 serves as the illumination light source.

Since the phosphor 1009 is applied to the front end face of the light guide fiber 902, the light emitting surface that serves as the illumination light source can be placed near an observation object. Accordingly, it is possible to emit the illumination light at a high light intensity. Further, the size can be reduced compared to typical LEDs.

Configuration of Insertion Part

Next, the configuration of the insertion part 11 will be disclosed. The above-described bending operation mechanism is not employed in the insertion part 11 of the following configurations (FIG. 11 to FIG. 15B). A peritoneal dialysis catheter k02 has a straight front end that is designed to be placed inside the abdominal cavity k03.

Configuration 1

First, Configuration 1 of the insertion part of one or more embodiments will be described referring to FIG. 11 and FIG. 12.

Figure 11:
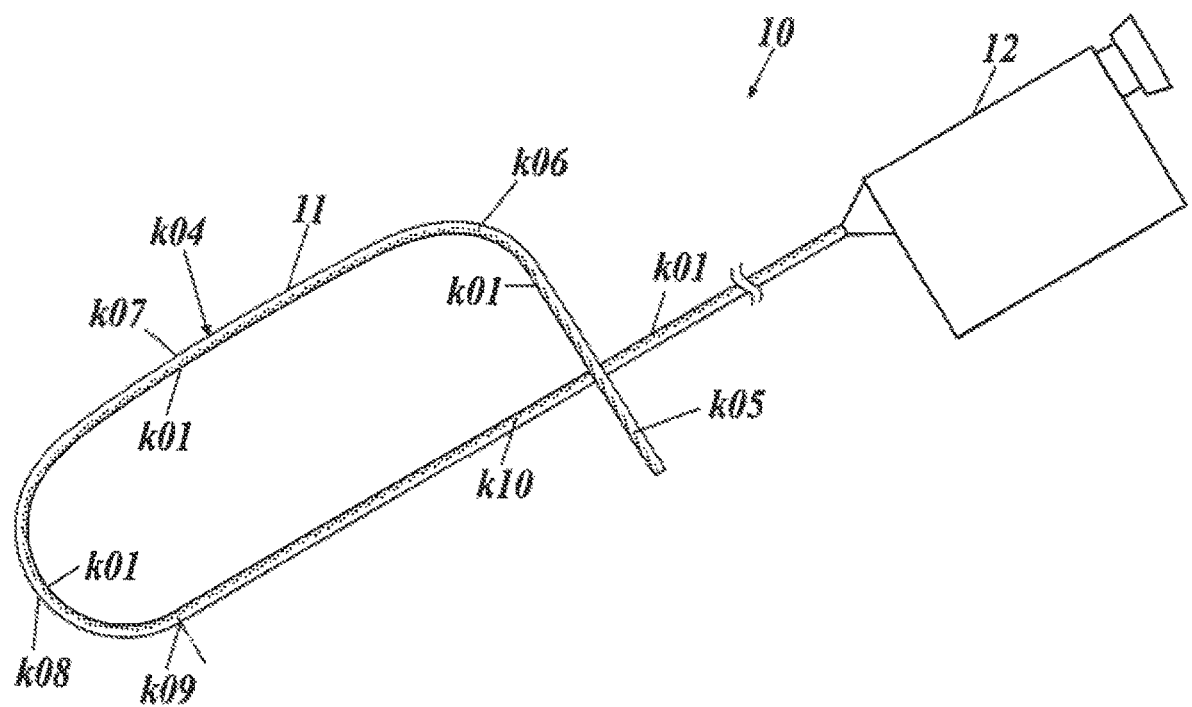
FIG. 11 is a schematic view of a laparoscopic device according to one or more embodiments of the present invention that illustrates a configuration thereof.

As illustrated in FIG. 11, the insertion part 11 is formed in a shape with a curved part in this configuration. A marker k01 that is detectable from the outside by means of X-ray or ultrasound (corresponding to the above-described "member 708") is provided along the center axis. In this configuration, the marker k01 is disposed at the side part along the inner side of the curvature of insertion part 11.

Figure 12:
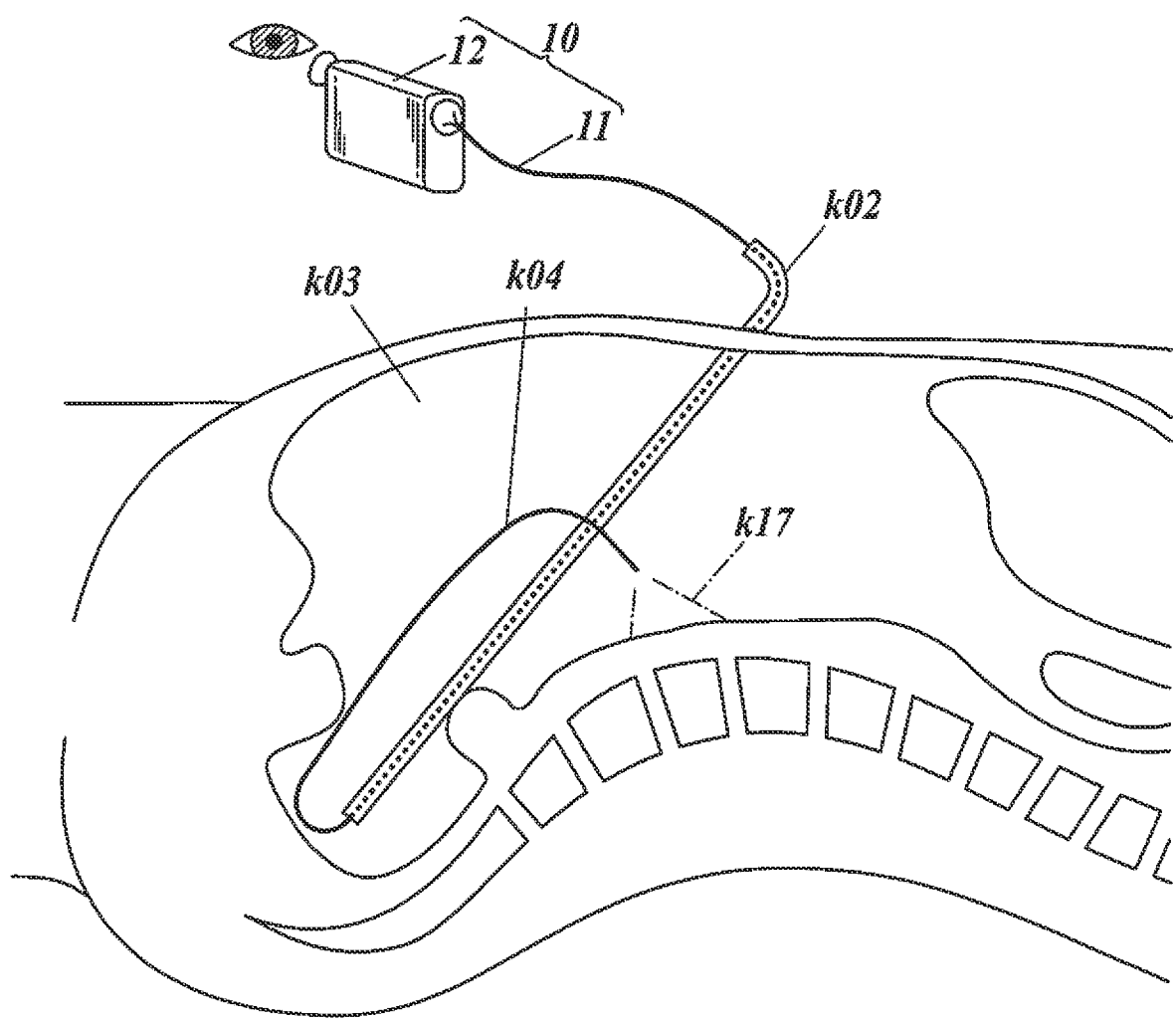
FIG. 12 is a schematic view of a scene where the laparoscopic device according to one or more embodiments of the present invention is in use.

According to one or more embodiments, this insertion part 11 and the operational part 12 connected to the base end of the insertion part 11 constitute the laparoscopic device 10 which is used for observing the abdominal cavity k03 by inserting the insertion part 11 through the peritoneal dialysis catheter k02 as illustrated in FIG. 12.

As illustrated in FIG. 12, a distal extended part k04 of the insertion part 11, which is extendable from the peritoneal dialysis catheter k02 into the abdominal cavity k03, is formed in a shape with a curved part that has an accumulated central angle of greater than 180° to 360°.

That is, the distal extended part k04 is bent over 180°, at which the direction of the front end along the center axis of the insertion part 11 is reversed, but not greater than a single loop (360°).

The curvature radius of the curved part of the distal extended part k04 may be uniform or varies. When the curvature radius varies, there may be a part having an infinite curvature radius (=straight part) in between.

In this configuration, the curved part of the distal extended part k04 is composed of a first curved part k06 and the second curved part k08 arranged in the written order from the front end as illustrate in FIG. 11. The distal extended part k04 further includes a straight part k07 with the straight center axis between the first curved part k06 and the second curved part k08 and a straight part k05 with the straight center axis at the distal side of the first curved part k06.

The first curved part k06 has a central angle within the range from 30° to 150°, and the second curved part k08 has a central angle within the range from 90° to 180°.

As illustrated in FIG. 11, the insertion part 11 is formed in a loop shape, and the front end part (straight part k05) of the distal extended part k04 crosses a straight part k10 that continues to the proximal end k09 of the distal extended part k04 of the insertion part 11.

The straight part in the distal side of the first curved part k06 is optional, and the first curved part k06 may be the most distal part without any straight part in the distal side of the first curved part k06. In this case, to form the loop structure as described above, the insertion part 11 may be formed in a loop shape such that the first curved part k06 crosses the straight part k10.

Configuration 2

Next, Configuration 2 of the insertion part of one or more embodiments will be described referring to FIG. 13A and FIG. 13B.

Figure 13A:
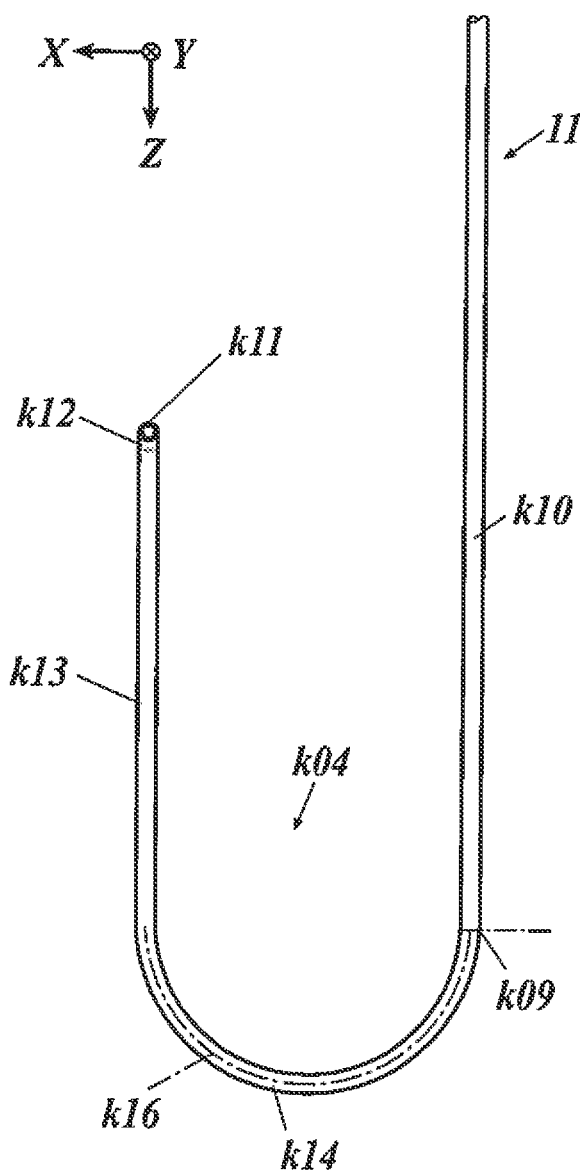
FIG. 13A is a schematic view of an insertion part of the laparoscopic device according to one or more embodiments of the present invention that illustrates a configuration thereof.
Figure 13B:
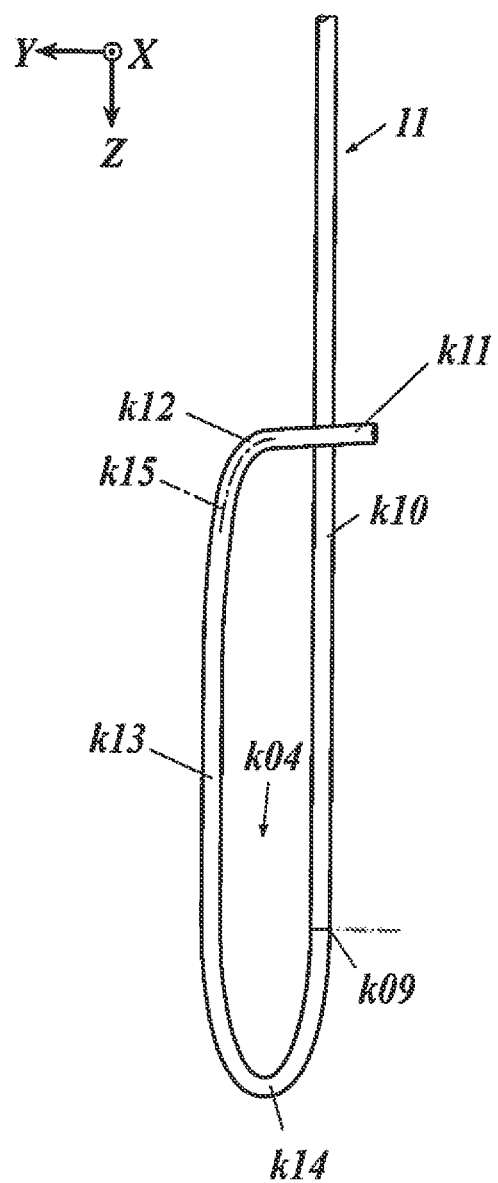
FIG. 13B is a schematic view of an insertion part of the laparoscopic device according to one or more embodiments of the present invention that illustrates a configuration thereof.

The distal extended part k04 of the insertion part 11, which is extendable from the peritoneal dialysis catheter k02 in the abdominal cavity 03, is composed of a straight part k11, a first curved part k12, a straight part k13 and a second curved part k14, which continue from the front end in the written order as illustrated in FIG. 13A and FIG. 13B.

The first curved part k12 has a central angle within the range from 30° to 150°, and the second curved part k14 has a central angle within the range from 90° to 180°.

Different from Configuration 1, the structure thereof is such that the plane containing the curved center axis k15 of the first curved part k12 (FIG. 13B) intersects with the plane containing the center curved axis k16 of the second curved part k14 (FIG. 13A). The intersecting angle is approximately 90° in one or more embodiments, but the angle may be suitably selected.

Insertion Procedure

The procedure of inserting the insertion part 11 of the above-described Configuration 1 or Configuration 2 through the peritoneal dialysis catheter k02 and observing the abdominal cavity k03 will de supplementarily described.

Fluid is suitably fed into the peritoneal dialysis catheter k02 and the abdominal cavity k03 by using the above-described joint 30 and the fluid feeding means 20. However, the illustration thereof is omitted in FIG. 12, FIG. 14A, FIG. 14B, FIG. 15A and FIG. 15B.

Figure 14A:
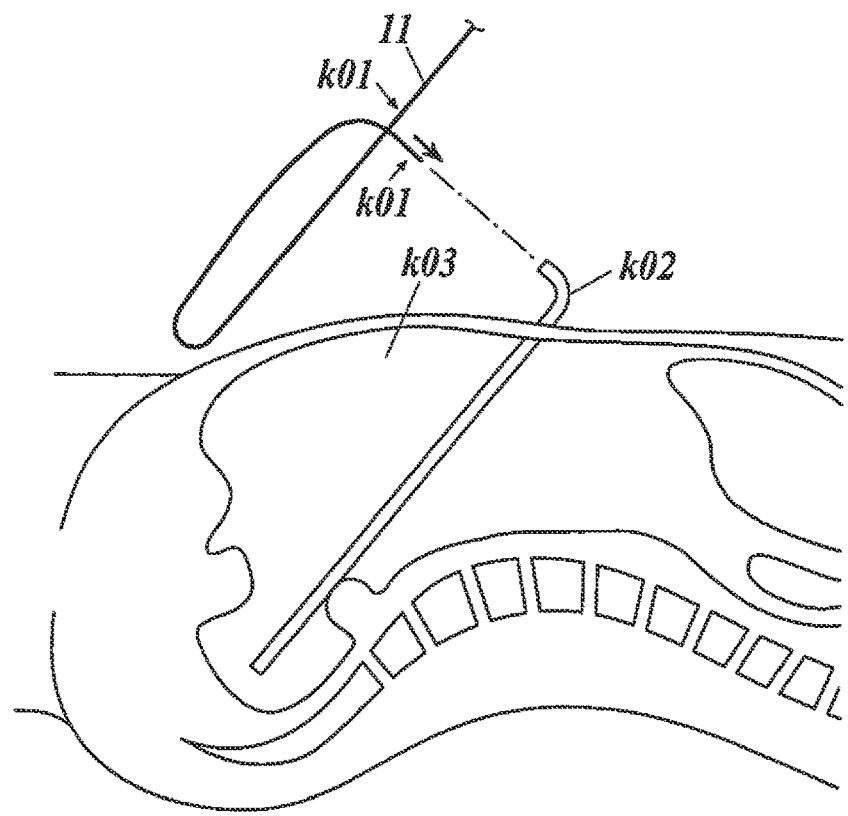
FIG. 14A is a schematic view of the laparoscopic device according to one or more embodiments of the present invention that illustrates an insertion procedure.
Figure 14B:
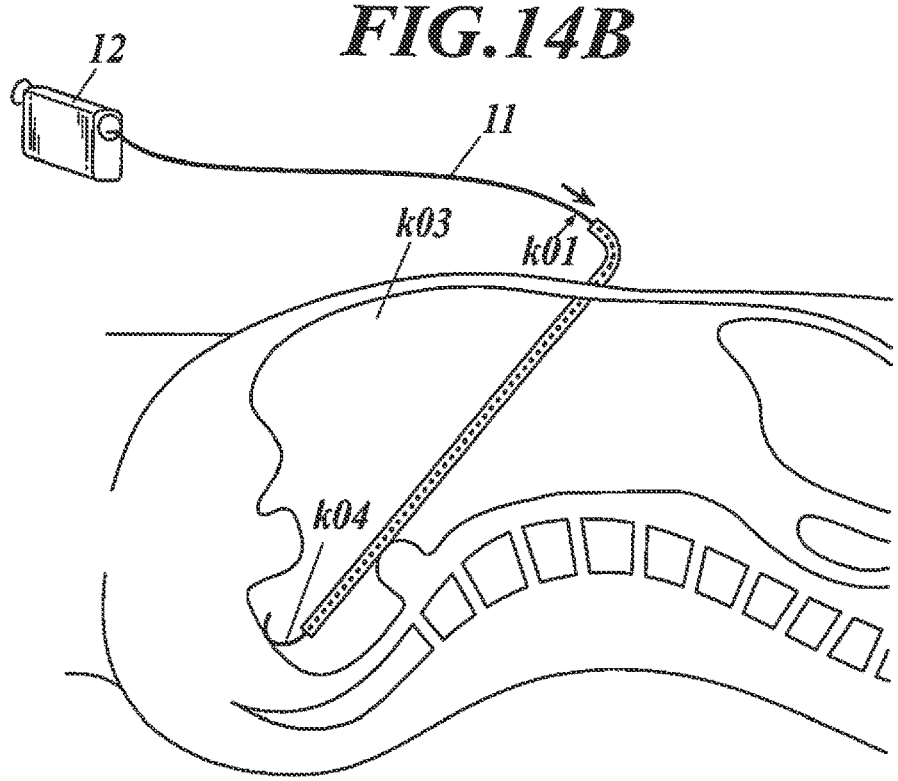
FIG. 14B is a schematic view of the laparoscopic device according to one or more embodiments of the present invention that illustrates the insertion procedure following FIG. 14A.

First, as illustrated in FIG. 14A and FIG. 14B, the insertion part 11 is inserted into the peritoneal dialysis catheter k02 from the front end. In FIG. 14A, FIG. 14B, FIG. 15A and FIG. 15B, the side where the marker k01 appears is indicated by an arrow. The insertion part 11 is inserted into the peritoneal dialysis catheter k02 while the marker k01 is directly checked and the angle about the axis of the insertion part 11 is adjusted to correspond to the curvature of the catheter k02 (FIG. 14A to FIG. 14B).

The insertion part 11 is curved in a no-load condition. However, since the insertion part 11 is elastic, it is stretched in the catheter k02 as it is inserted.

As illustrated in FIG. 14B, the first curved part (k06, k12) of the distal extended part k04 curves as it extends from the front end opening of the catheter k02. To make the distal extended part k04 curve in a direction suitable for bringing it to the upper part of the abdominal cavity k03, the curved condition of the distal extended part k04 is checked in an X-ray photographic image or an ultrasonic photographic image in which the marker k01 is detected, and the angle about the axis of the insertion part 11 is adjusted. Then, the insertion part 11 is further inserted (FIG. 14B to FIG. 15A to FIG. 15B).

Figure 15A:
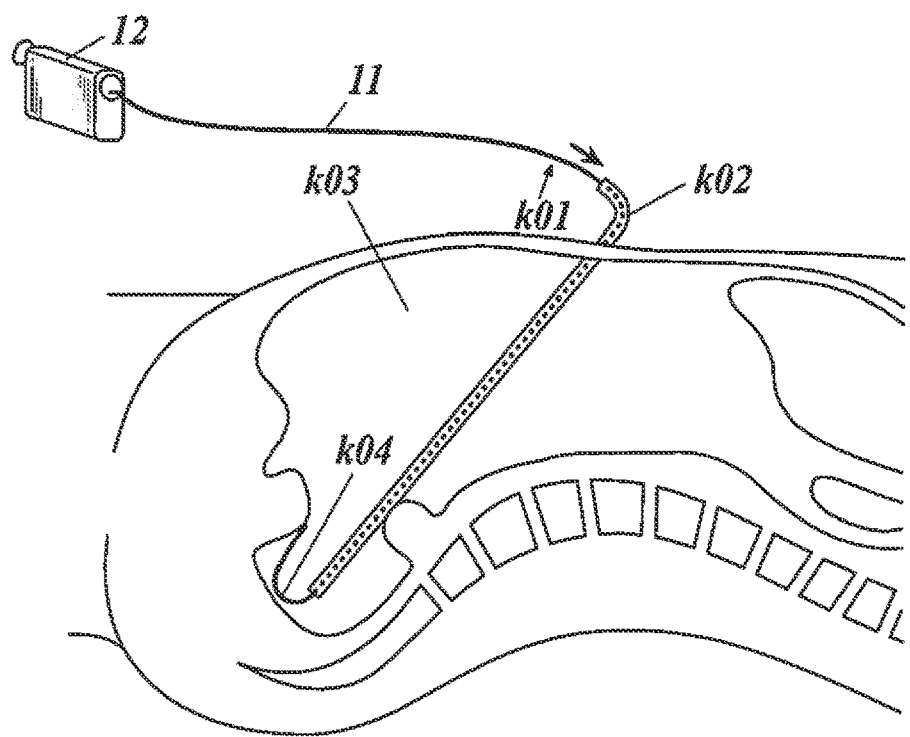
FIG. 15A is a schematic view of the laparoscopic device according to one or more embodiments of the present invention that illustrates the insertion procedure following FIG. 14B.
Figure 15B:
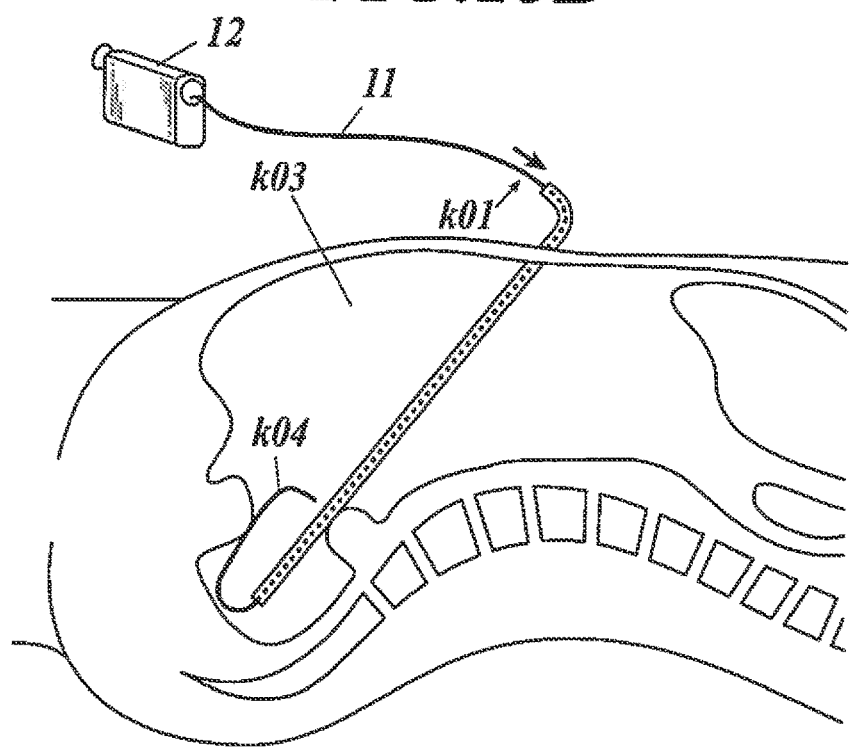
FIG. 15B is a schematic view of the laparoscopic device according to one or more embodiments of the present invention that illustrates the insertion procedure following FIG. 15A.

The X-ray photographic image or the ultrasonic photographic image in which the marker k01 is detected is occasionally checked, and the angle about the axis of the insertion part 11 is adjusted so that the front end of the distal extended part k04 is opposed to an observation object when the second curved part (k08, k14) fully comes out of the catheter k02. Then, the insertion part 11 is further inserted (FIG. 15B to FIG. 12). For example, the insertion part 11 is placed so that the upper part of the small intestine is included an endoscopic field k17 as illustrated in FIG. 12. It is needless to say that useful abdominal cavity images are obtained also during the insertion process.

Thereafter, the endoscopic field k17 is changed by an operation of rotating the insertion part 11 around the axis or pushing/pulling the insertion part 11 in the axial direction, so that the observation is made in a wider area.

After the observation, the insertion part 11 is pulled out of the catheter k02, the components that are connected to the peritoneal dialysis catheter k02 for the endoscopic observation, such as the joint 30, are removed so that the catheter is in a normal connection state after a peritoneal dialysis. The endoscopy is thus complete.

As described above, the laparoscopic device of one or more embodiments can be inserted through a peritoneal dialysis catheter and extended from the peritoneal dialysis catheter in the abdominal cavity, and the front end thereof can be guided to a location opposed to the great omentum and the small intestine and placed in an angle in which the great omentum and the small intestine are sufficiently included in the field of view.

Embodiment B

FIG. 1 to FIG. 10C and FIG. 16 to FIG. 30E are referenced in this section.

Overview of System Configuration

First, the overview of a whole endoscopic system of one or more embodiments will be described.

As illustrated in FIG. 1 to FIG. 3, the endoscopic system 1 of one or more embodiments include an endoscope 10, a fluid feeding means 20 and a joint 30. FIG. 1 illustrates the state in which the joint 30 and the other components are separated from each other. FIG. 2 illustrates the state in which the other components are connected with the joint 30, and the endoscope is inserted. FIG. 3 illustrates the state in which a conversion connector 40 is further connected.

The endoscope 10 is composed of an insertion part 11 and an operational part 12. The insertion part 11 is composed of an imaging optical system and an illumination optical system, which are covered with a protection tube.

For the imaging optical system, an imaging lens disposed at the front end of the insertion part 11 is used as well as an image fiber or an imaging element that transmits or takes an image formed by the imaging lens.

For the illumination optical system, a solid light emitting element that is disposed at the front end of the insertion part 11 or a light guide fiber that guides light from a light source disposed in the operational part 12 to the front end of the insertion part 11 is used.

The protection tube encloses the imaging optical system and the illumination optical system so as to constitute the exterior of the insertion part 11. The protection tube is made of a material with moderate flexibility and high surface slipperiness.

Further, hydrophilic coating may be provided on the outer surface of the material of the protection tube (exterior tube) to improve the surface slipperiness.

The operational part 12 is connected to the base end of the insertion part 11. In particular, the insertion part 11 and the operational part 12 are detachably connected with each other. With this configuration, it is possible to wash and sterilize only the insertion part 11 of the endoscope 10 by detaching the insertion part 11 from the operational part 12 or to use a disposable (non-reusable) insertion part 11 in order to maintain the quality and the hygiene.

That is, while catheters and endoscopes that are inserted into the body cavity are sterilized before use in order to prevent an infection, the component to be sterilized can be reduced to only the insertion part 11. The sterilization methods that can be used include EOG sterilization, autoclaving, γ-ray sterilization and the like.

Repetitive sterilization of the insertion part 11 may degrade the properties of the slip coating applied to the outer circumferential face of the protection tube. A connector part may be provided so that the insertion part 11 and the operational part 12 of the endoscope 10 are separable from each other, and the insertion part 11 is configured to be disposable after each use. This enables always supplying the insertion part 11 with good slipperiness, which facilitates an insertion into an indwelling catheter 100. In contrast to typical reusable endoscopes, being disposable eliminates the risk of infection caused by an insufficient wash or sterilization.

The operational part 12 is a handheld device that is held by an operator and is used for operations of the insertion part 11 such as back and forward movements and rotation around the axis. The operational part 12 also serves as a base end unit in which an optical or electrical component for lighting or imaging through the insertion part 11 is housed.

A bending mechanism may be further provided for a bending operation of the insertion part 11 by means of a wire coupled to the protection tube or the like. In this case, operation members such as a dial and a lever are disposed in the connector part at the base end of the insertion part 11 or in the operational part 12.

It is advantageous that the bent insertion part 11 has a curved shape. That is, the insertion part 11 originally has a curved shape in a no-load condition. The curved shape is such that the insertion part 11 curves in the vicinity of the front end within the range from 30° to 180°. By an operation on the operational part 12 of rotating the insertion part 11 around the axis, it is possible to turn the front end of the insertion part 11 toward the distal part of the indwelling catheter 100 in a curved part such as a bent part 101 and a spiral part 102 of the indwelling catheter 100. This facilitates bringing the insertion part 11 to the distal end 104 of the indwelling catheter 100. Further, by an operation on the operational part 12 of rotating the insertion part 11 around the axis, it is possible to change the view direction so as to observe a wider area. In this regard, it is desirable that the curvature of the insertion part 11 has an optimal specific shape according to the positional relationship between the distal end 104 of the indwelling catheter 100 and an observation subject and to the view angle of the imaging optical system of the insertion part 11. For example, in the case where the view angle of the imaging optical system is 60° in all directions and the curvature is set to 30°, the area ahead in the axial direction is always included in the field of view even when the insertion part 11 is rotated around the axis. Accordingly, the view of the distal part of the indwelling catheter, to which the insertion part 11 is inserted, is ensured during the operation.

It is advantageous that the insertion part 11 is configured such that the flexural rigidity decreases toward the front end. This facilitates inserting the insertion part 11 because the insertion part 11 can be easily forwarded even in a sharply bent part of the indwelling catheter 100 and the part with comparatively high rigidity near the base end facilitates transmitting a force for the insertion in the axial direction.

It is advantageous that the insertion part 11 includes a member that is disposed at a predetermined position and is detectable by means of X-ray or ultrasound. This is because when the insertion part 11 is inserted into the indwelling catheter 100, the insertion depth of the insertion part 11 can be checked, and the front end of the insertion part 11 can thereby be guided to a predetermined position at high positional accuracy.

For the fluid feeding means 20, an infusion bag, a syringe, an infusion pump, a syringe pump and the like for medical use are used. For example, an infusion bag is connected to the joint 30 via an infusion tube 21. When an infusion bag is used, an infusion pump can be used for mechanically feeding fluid. The infusion pump may be of roller type, finger type, volumetric type or the like. Instead of the infusion bag, a syringe is connected to the joint 30 directly or via the infusion tube 21. When the syringe is used, a syringe pump can be used for mechanically feeding fluid.

The joint 30 includes a first connector part 31, a second connector part 32, an insertion opening 33 and a communication channel 34.

The first connector part 31 is connected to the proximal end 103 of the indwelling catheter 100. The second connector part 32 is connected to the output end 22 of the fluid feeding means 20. The insertion opening 33 is used for inserting the insertion part 11.

The communication channel 34 is communicated to the first connector part 31, which is further communicated to the second connector part 32 and the insertion opening 33 via a confluence part 34a. The communication channel 34 is a channel member having a trifurcate structure in the confluence part 34a. The communication channel from the first connector part 31 to the insertion opening 33 is formed in a straight shape. This facilitates inserting the insertion part 11.

The joint 30 includes a check valve 35 between the insertion opening 33 and the confluence part 34a for preventing fluid from leaking though the insertion opening 33.

As illustrated in FIG. 2 and FIG. 3, the joint with the above-described configuration allows the insertion part 11 to enter from the insertion opening 33 into the communication channel 34 to pass through the confluence part 34a and the first connector part 31 to enter the indwelling catheter 100 connected to the first connector part 31. Further, the joint 30 allows fluid fed from the fluid feeding means 20 connected to the second connector part 32 to pass through the confluence part 34a and the first connector part 31 to flow into the indwelling catheter 100 connected to the first connector part 31.

Accordingly, in the joint 30 connected to the indwelling catheter 100 and the indwelling catheter 100, the fluid from the fluid feeding means 20 can flow around the insertion part 11 in the direction toward the body cavity. The fluid reduces the friction between the insertion part 11 and the inner wall of the indwelling catheter 100. That is, the contact friction between the inner surface of the indwelling catheter 100 and the outer surface of the insertion part 11 can be reduced by feeding the fluid such as saline to the gap between the indwelling catheter 100 and the insertion part 11, and it is therefore possible to insert the insertion part 11 into the indwelling catheter 100 in a slippery condition. Further, the fluid makes a force of moving the insertion part 11 in the direction toward the body cavity, which facilitates inserting the insertion part 11 into the indwelling catheter 100.

For the fluid fed from the fluid feeding means 20, a biocompatible fluid is used. For example, when the indwelling catheter 100 is a peritoneal dialysis catheter, peritoneal dialysis solution can be used. A lubricant for a urethral catheter can also be used. Further, saline and the like can also be used. In addition to the biocompatibility, fluid that improves the slipperiness between the insertion part 11 and the inner wall of the indwelling catheter 100 is selected.

The first connector part 31 is connected to the proximal end 103 of the indwelling catheter 100. There are the following two methods of adapting the first connector part 31 to a variety of indwelling catheters 100 with different sizes, shapes and attached connector parts of the proximal end 103.

One method involves providing many types of joints 30 with different structures of the first connector part and selecting a joint 30 that includes a first connector part 31 connectable to the proximal end 103 of the indwelling catheter 100. However, the resource efficiency is low in this method.

The other method involves using a conversion connector 40 as illustrated in FIG. 3. The conversion connector 40 includes a third connector part 41 at one end 40a thereof that is connected to the first connector part 31 and also includes a fourth connector part 42 at the other end 40b thereof that is connectable to a counterpart structure different from the counterpart structure connectable to the first connector part 31. The adaptation can be achieved by providing various types of conversion connectors 40 with fourth connector parts 42 of different structures.

Configuration of Connector

Examples of connectors that can be used in the proximal end 103 of the indwelling catheter 100, the first connector part 31, the second connector part 32, the third connector part 41, the fourth connector part 42 and the output end 22 of the fluid feeding means 20 will be described.

Such connectors include a connector for peritoneal dialysis as illustrated in FIG. 4A, a luer connector as illustrated in FIG. 4B and a screw-in connector as illustrated in FIG. 4C. They are designed to connect a tube 401 and a tube 402 to each other. A spike connector as illustrated in FIG. 4D is designed to connect a tube 404 integrally formed with an infusion bag 403 to a tube 405.

The connector for peritoneal dialysis as illustrated in FIG. 4A includes a connector body part (male) 406, a locknut 407, a connector part (female) 408. The luer connector as illustrated in FIG. 4B includes a connector part (female) 409 and a connector part (male) 410. The screw-lock connector as illustrated in FIG. 4C includes a connector part (female) 411 and a connector part (male) 412. The spike connector as illustrated in FIG. 4D includes a connector part (female) 413 and a connector part (male) 414.

When the tube 401 in FIG. 4A is the indwelling catheter 100 and the connector part (female) 408 is employed as the first connector part 31, the indwelling catheter 100 is connectable to the joint 30. However, in this case, the first connector part 31 is connectable to neither connector part (female) 409 nor the connector part (female) 411. The conversion connector 40 is used. When the conversion connector 40 has the third connector part 41 that is formed in the shape of the connecting end of the connector part (male) 406 and the fourth connector part 42 that is formed in the shape of the connecting end of the connector part (male) 410, the first connector part 31 can be connected to the connector part (female) 409 via the conversion connector 40. Similarly, when the conversion connector 40 has the third connector part 41 that is formed in the shape of the connecting end of the connector part (male) 406 and the fourth connector part 42 that is formed in the shape of the connecting end of the connector part (male) 412, the first connector part 31 can be connected to the connector part (female) 411 via the conversion connector 40.

Such conversion connectors can also be used between the fluid feeding means 20 and the second connector part 32. FIG. 5 illustrates an example of a connector part 502 that is connected to a syringe 501. When the connector part 502 is employed as the second connector part 32, the syringe 501 can be connected without an infusion tube.

Another proposal is a snap-fit connector as illustrated in FIG. 6. A tube 601 is connected to an end of the connector part in FIG. 6. The tube 601 corresponds to the indwelling catheter 100 or the infusion tube 21. The other end 602 is connected to a joint 30 in a snap-fit manner. The counterpart structure to receive the other end 602 in the snap-fit manner is formed in the first connector part 31 or the second connector part 32.

Configuration of Endoscope

Some configurations of the endoscope 10 will be described.

Configuration 1

FIG. 7A and FIG. 7B illustrate a configuration of the endoscope of one or more embodiments in which an imaging element 701 is used for the imaging optical system and a solid light emitting element 702 is used for the illumination optical system.

An endoscope 10A of FIG. 7A and FIG. 7B is composed of an insertion part 11A and an operational part 12A. The insertion part 11A is composed of an imaging optical system and an illumination optical system, which are covered with a protection tube 703. For the imaging optical system, an imaging lens 704 disposed at the front end of the insertion part 11A is used as well as an imaging element 701 that takes an image formed by the imaging lens 704 and an electric cable 705. For the imaging element 701, an electronic device that can perform photoelectric conversion such as a CCD (charge coupled device) or a CMOS imaging sensor is used. The electric cable 705 is provided to supply electric power to the imaging element 701 and the solid light emitting element 702 and to transmit a video signal taken by the imaging element 701. The solid light emitting element 702 is constituted by an LED (light emitting diode) in this configuration.

The protection tube 703 encloses the imaging optical system and the illumination optical system so as to constitute the exterior of the insertion part 11A. The protection tube 703 is made of a material with moderate flexibility and high surface slipperiness.

The operational part 12A is connected to the base end of the insertion part 11A. In particular, the insertion part 11A includes a connector part 722 at the base end so that it is detachable from the operational part 12A. The operational part 12A is a handheld device that can be held by an operator and is used for operations of the insertion part 11A such as backward and forward movements and rotations. The operational part 12A also serves as a base end unit that houses optical or electrical equipment for the lighting and imaging by the insertion part 11A.

In addition, a bending mechanism that bends the insertion part 11A by means of a wire 706 coupled to the protection tube 703 is provided. An operation dial 707 is provided in the connector part 722 as the operation member thereof.

In the protection tube 703, a member (detection mark) 708 detectable by means of X-ray or ultrasound is embedded at a predetermined position.

The operational part 12A includes a video processor 709 that receives a video taken by the imaging element 701 through the electric cable 705 and outputs it to a video output terminal 710 after necessary image processing. The video is displayed on a video display monitor 711 connected to the video output terminal 701. The video output from the video output terminal 710 can be recorded on a recorder 712.

A light source driver 713 applies a drive current to the solid light emitting element 702 through the electric cable 705 so that the solid light emitting element 702 emits light. An operation member such as a light intensity adjustment knob 714 is provided in the operational part 12A so that the light intensity of the solid light emitting element 702 can be adjusted. The electrically driven part of the operational part 12A including the video processor 709 and a light source driver 713 is powered by a battery 716 loaded in a loading part 715 of the operational part 12A or by an AC power source connected through a power cable 717, and a power switch 718 is provided in the operational part 12A. The battery level of the battery 716 is indicated on an indicator 721.

Further, a channel opening 719 is formed in the connector part 722. The channel opening 719 is communicated with a channel 720.

FIG. 8 illustrates a scene in use. For example, the video display monitor 711 and the recorder 712 are placed on a table 801, and the syringe 802 and the infusion pump 803 as the fluid feeding means 20 are further mounted according to need. The syringe 802 and the infusion pump 803 are connected to the joint 30 via the infusion tube 21. Further, the indwelling catheter 100 and the joint 30 are connected to each other. Thereafter, infusion is started, and the fluid is fed to the indwelling catheter 100. Simultaneously with or after starting the infusion, the insertion part 11A of the endoscope 10A is inserted through the insertion opening 33 of the joint 30. The insertion part 11A is inserted to a deep part while the location and position of the insertion part 11A is being monitored by detecting the member 708 by means of an X-ray or ultrasonic detector 804, in which the insertion part 11A is bent by using the operation dial 707 according to need. While the front end of the insertion part 11A is located inside the indwelling catheter 100, it is possible to observe the inside of the indwelling catheter 100, in which the insertion part 11A can be bent according to need. After the front end of the insertion part 11A gets out of the distal end 104 of the indwelling catheter 100, it is possible to observe the body cavity where the indwelling catheter 100 is placed, in which the insertion part 11A can be bent according to need. Further, a forceps 805 is inserted through the channel opening 719 and used according to need.

Configuration 2

FIG. 9A and FIG. 9B illustrates a configuration of the endoscope of one or more embodiments in which an image fiber 901 is used for the imaging optical system and a light guide fiber 902 is used for the illumination optical system.

An endoscope 10B of FIG. 9A and FIG. 9B is composed of an insertion part 11B and an operational part 12B. The same reference signs are denoted to the same components as those in FIG. 7A and FIG. 7B.

For the imaging optical system, an imaging lens (see FIG. 11A and FIG. 11B, reference sign 904) that is held by a lens frame 903 disposed at the front end of the insertion part 11B is used as well as the image fiber 901 that transmits an image formed by the imaging lens.

For the illumination optical system, the light guide fiber 902 is used.

The operational part 12B is connected to the base end of the insertion part 11B. The image fiber 901 is optically coupled to a relay optical system 905 disposed in the operational part 12B. The relay optical system 905 relays an image between the image fiber 901 and an eyepiece lens 906 so that the image transmitted from the image fiber 901 can be visually observed through an eyepiece unit 907.

In the operational part 12B, an illumination light source 908 is disposed. The light from the light source 908 enters the light guide fiber 902 through a coupling lens 909, is guided to the front end face of the insertion part 11B by the light guide fiber 902 and is casted to the observation object.

To output the image transmitted by the image fiber 901 to the video display monitor 711, a signal conversion adapter 910 is connected to the eyepiece unit 907. The signal conversion adapter 910, which includes an imaging lens 911, an imaging element 912, a video processor 913 and a video output terminal 914, outputs an image from the eyepiece lens 906 to the video output terminal 914 in the form of a video signal.

As described above, the image fiber 901 is used for the imaging optical system, which is constituted by thousands of optical fibers formed in a bundle. A GRIN lens is provided at the front end of the image fiber 901, which is fixed in close contact with the image fiber 901 and serves as the imaging lens.

For the illumination optical system, the light guide fiber 902 is provided to propagate light from the illumination light source to an observation object, which is constituted by hundreds of optical fibers formed in a bundle.

A flexible protection tube 703 is provided around the imaging optical system and the illumination optical system to avoid a contact between the living body and the optical components.

The optical fibers of the image fiber and the light guide fiber may be made of any material that has a transmittance and a color suitable for the usage, which can be selected from multi-component glass, silica glass and plastic (polymethylmethacrylate, polystyrene, styrene acrylonitrile, polyurethane and the like). The diameter, the NA, the number and the like of the optical fibers used may be suitably selected as long as they can be correctly assembled.

For the imaging optical system, a photo-electric element used in electronic endoscopes or the like may be used instead of the image fiber as described in Configuration 1. In this case, it is possible to obtain an image with a higher quality than in the case using the image fiber.

Configuration 3

Another possible configuration of one or more embodiments is a combination of the imaging optical system of Configuration 1 with the illumination optical system of Configuration 2.

Configuration 4

Another possible configuration of one or more embodiments is a combination of the imaging optical system of Configuration 2 with the illumination optical system of Configuration 1.

Configuration 5

The operational part may have the function of the video display monitor and/or the recorder in FIG. 7A or the like. For example, a thin image display device 1001 is installed in an operational part 12C as illustrated in FIG. 10A. Further, a writer 1003 for a recording medium 1002 is installed in the operational part 12C as illustrated in FIG. 10B. In the illustrated example, an insertion part 11C of FIG. 10B includes a connector part 1004 and an image fiber 1005, and the operational part 12C includes an imaging lens 1006, an imaging element 1007 and a video processor 1008.

Configuration 6

As illustrated in FIG. 10C, the illumination optical system may be configured such that a phosphor 1009, which is applied to the front end face of the light guide fiber 902 located at the front end face of the insertion part 11B, is irradiated with excitation light guided from a light source 1010 through the light guide fiber 902, the phosphor 1009 is thereby exited, and the light generated by the excitation is casted from the phosphor 1009 to an observation object as illumination light. That is, the phosphor 1009 serves as the illumination light source.

Since the phosphor 1009 is applied to the front end face of the light guide fiber 902, the light emitting surface that serves as the illumination light source can be placed near an observation object. Accordingly, it is possible to emit the illumination light at a high light intensity. Further, the size can be reduced compared to typical LEDs.

Embodiments with Guide Catheter

Next, one or more embodiments using a guide catheter k01 will be described. For an indwelling catheter, a peritoneal dialysis catheter k02 with a straight front end k03 is used, which is designed to be placed in the abdominal cavity.

Configuration 1

First, an endoscopic system using Configuration 1 of one or more embodiments will be described.

Figure 16:
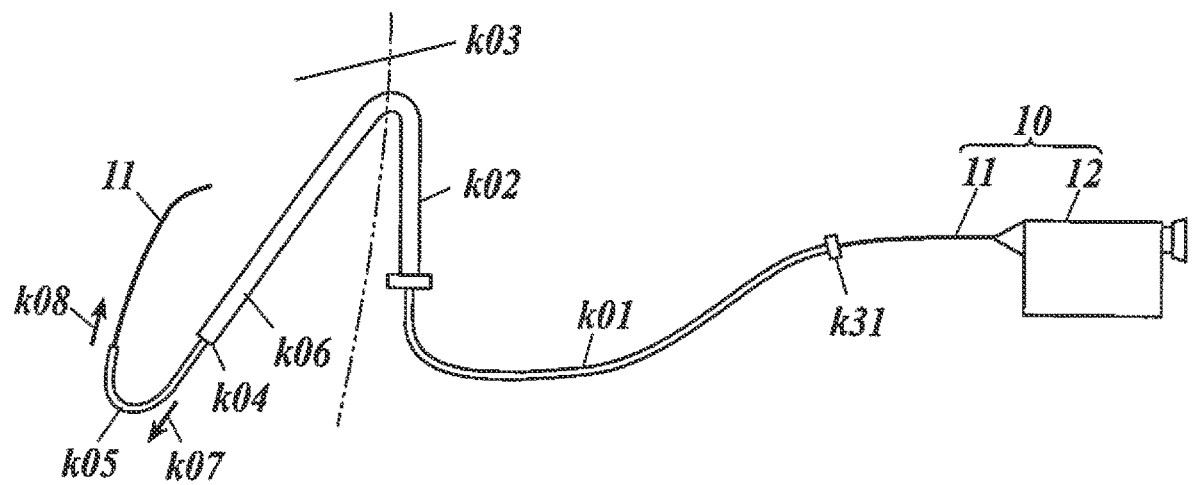
FIG. 16 is a schematic overview of an endoscopic system according to one or more embodiments of the present invention.

As illustrated in FIG. 16, the endoscopic system includes a guide catheter k01. The guide catheter k01 guides the insertion part 11 that is inserted in the guide catheter k01. Further, the guide catheter k01 is inserted through a catheter k02, and the curvature of a distal extended part k05 thereof extending from the terminal opening k04 of the catheter k02 provides a function of guiding the insertion part 11 in a direction k08 different from a direction k07 guided by a terminal part k06 of the catheter k02.

To achieve the guiding function of the guide catheter k01, the curvature of the distal extended part k05 is originally formed as the curved shape of the distal extended part k05, or the curvature is formed by a bending mechanism that is operated during use for bending the distal extended part k05. The front end of the insertion part 11 also has an originally formed curved shape or the above-described bending mechanism that is operated during use through the wire 706, the operation dial 707 and the like.

The former curved shape can be formed by utilizing the thermoplasticity of the resin material of the guide catheter k01. The same applies to the insertion part 11.

Figure 17A:
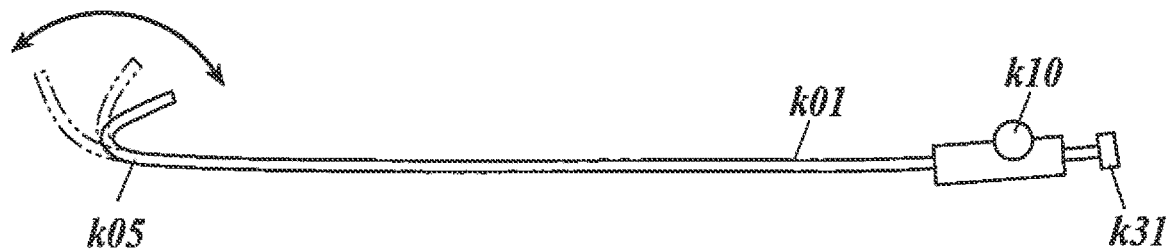
FIG. 17A is a schematic view of an example of a bending mechanism of a guide catheter according to one or more embodiments of the present invention.
Figure 17B:
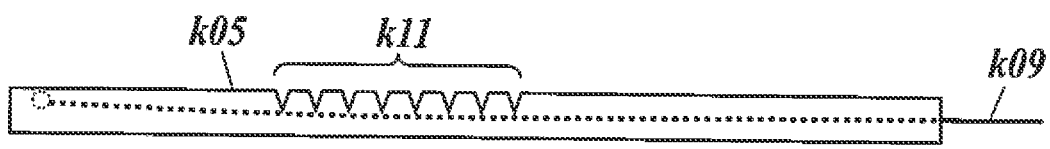
FIG. 17B is a schematic view of the bending part of the guide catheter of FIG. 17A that illustrates the details thereof.
Figure 17C:
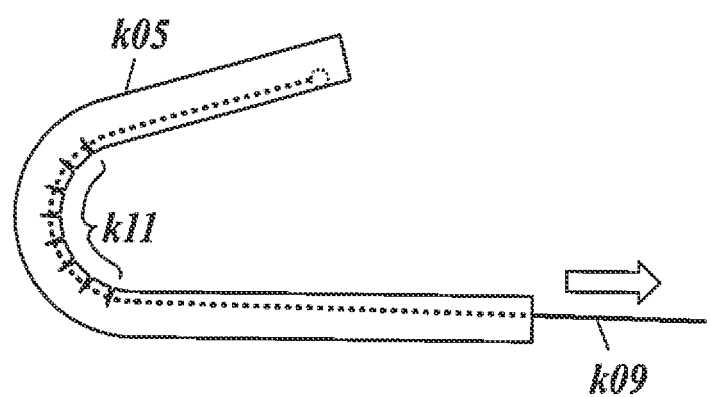
FIG. 17C is a schematic view of the bending part of the guide catheter of FIG. 17A that illustrates the details thereof.

FIG. 17A, FIG. 17B and FIG. 17C illustrate examples of the latter bending mechanism. For example, as illustrated in FIG. 17A, FIG. 17B and FIG. 17C, the bending mechanism bends the guide catheter k01 by means of a wire k09 coupled to the guide catheter k01. In the vicinity of the base end of the guide catheter k01, an operation dial k10 is provided as the operation member thereof. The wire k09 is coupled to the operation dial k10 so that the wire k09 can be operated through the operation dial k10. To ease the bending operation, grooves k11 may be provided in the inner side of the bent part of the guide catheter k01 in the circumferential direction.

Configuration 2

Next, Configuration 2 of the endoscopic system of one or more embodiments will be described, in which the fluid feeding means 20 and the joint 30 are used.

Figure 18:
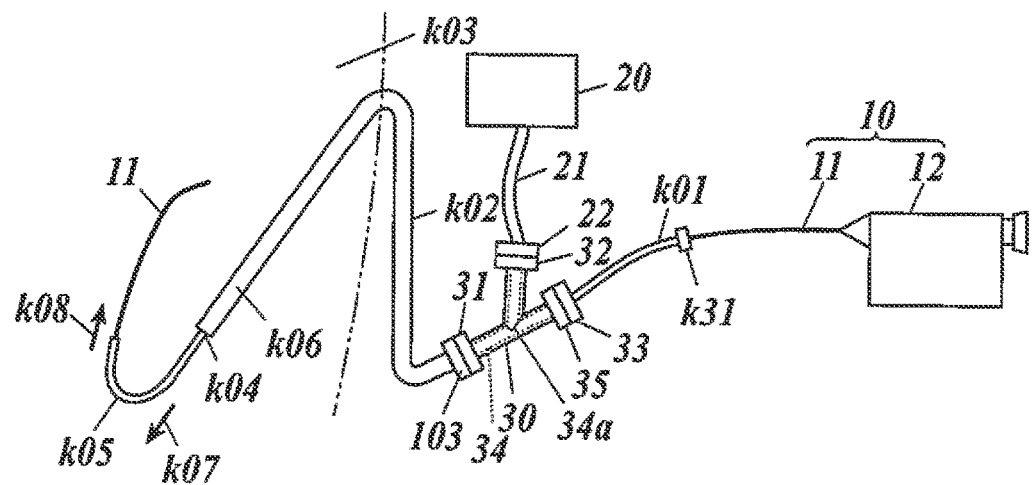
FIG. 18 is a schematic overview of the endoscopic system according to one or more embodiments of the present invention.

As illustrated in FIG. 18, the above-described fluid feeding means 20 and the joint 30 are used. The guide catheter k01 is inserted from an insertion opening 33 of the joint 30. Also in this configuration, the joint 30 includes a check valve 35 between the insertion opening 33 and the confluence part 34a that prevents fluid from leaking through the insertion opening 33.

The joint 30 further includes a fixing mechanism that fixes the guide catheter k01 inserted through the insertion opening 33 with respect to the joint 30. The fixing mechanism may be configured such that the check valve 35 frictionally engages with the outer circumferential face of the guide catheter k01 such as a hemostasis valve so as to seal it.

The guide catheter k01, which has hydrophilic coating on the outer surface, wets with the fluid fed from the fluid feeding means 20 into the joint 30 and the catheter k02, and the outer surface of the guide catheter k01 is thereby slippery against the inner surface of the joint 30 and the inner surface of the catheter k02. This facilitates the insertion of the guide catheter k01.

Configuration 3

Next, Configuration 3 of the endoscopic system of one or more embodiments will be described, in which an extension catheter k12 is further added to the above-described Configuration 2.

The extension catheter k12 is constituted by a tube for extending the distance between the joint 30 and the catheter k02.

Figure 19:
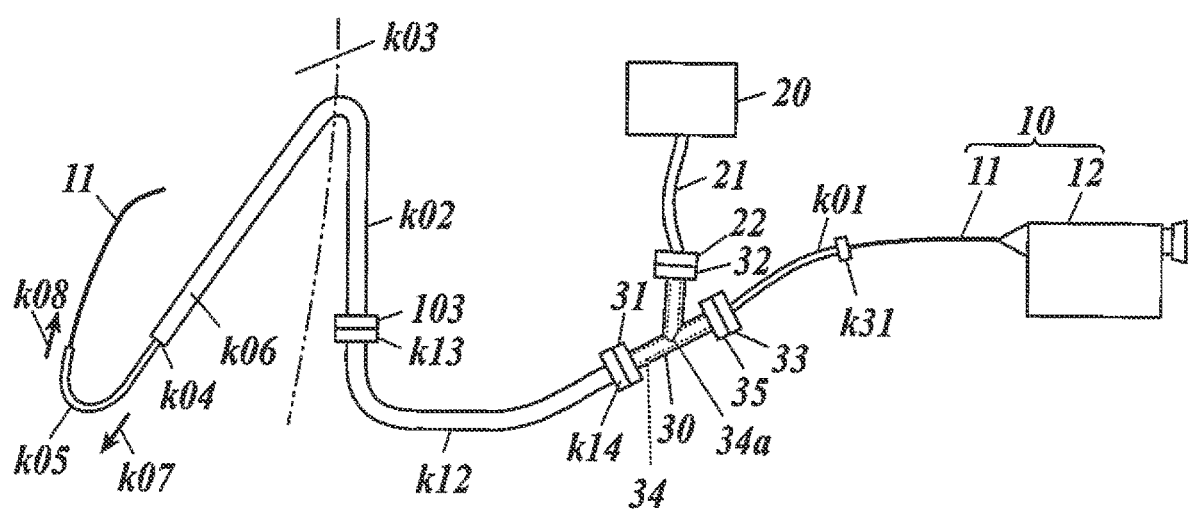
FIG. 19 is a schematic overview of the endoscopic system according to one or more embodiments of the present invention.

As illustrated in FIG. 19, the extension catheter k12 is connected between the catheter k02 and the joint 30. That is, a connector k13 at one end of the extension catheter k12 is connected to the proximal end 103 of the catheter k02, and a connector k14 at the other end is connected to the first connector part 31 of the joint 30.

This enables performing a connection of the fluid feeding means 29 or an insertion of the guide catheter k01 and the like with the joint 30 away from the patient body where the catheter k02 is placed. Various types of extension catheters k12 with different lengths may be used corresponding to various types of catheters k02 with different lengths so that the total length of the catheter k02 and the extension catheter k12 becomes the same. As a result, it is possible to keep the insertion of the guide catheter k01 required for a certain length of the distal extended part k05 at a certain length.

Usage

Next, modes of the usage of one or more embodiments will be described with the system of Configuration 3 as an example.

Usage 1

Usage 1 will be described.

First, the guide catheter k01 is inserted to the catheter k02 so that the distal extended part k05 is extended from the terminal opening k04 of the catheter k02. During the insertion, fluid is fed from the fluid feeding means 20. The distal extended part k05 of the guide catheter k01 has such a flexibility that allows it to be stretched in a straight shape in the catheter k02 during the insertion but to return to the original shape with the curved front end when it comes out of the catheter k02.

Then, the insertion part 11 of the endoscope is inserted in the guide catheter k01. During the insertion, fluid is similarly fed from the fluid feeding means 20. The front end of the insertion part 11 is guided from the distal opening of the guide catheter k01 in a predetermined direction k08. By further sending the insertion part 11 with the guide in the predetermined direction k08, it is possible to bring the front end of the insertion part 11 to the upper part of the abdominal cavity k03 where there is an observation point. The front end of the insertion part 11 is placed and directed to a desired observation point, and an observation is made.

Usage 2

Usage 2 will be described referring to FIG. 20A, FIG. 20B and FIG. 20C.

Figure 20A:
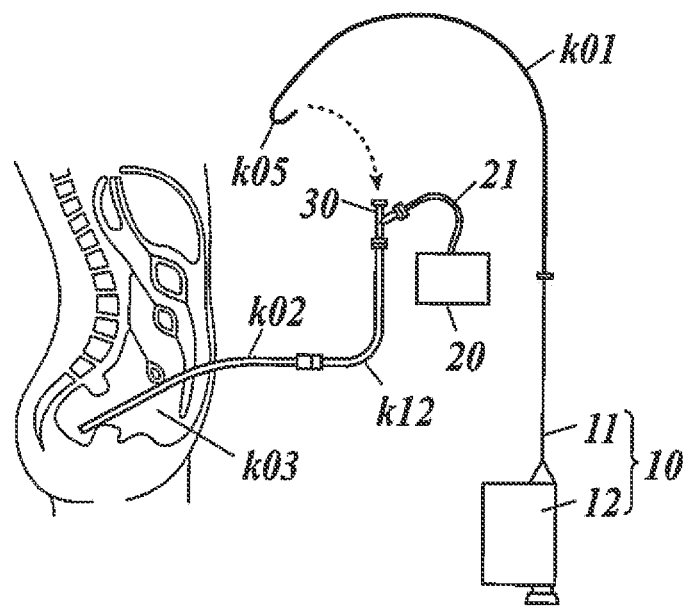
FIG. 20A is a schematic overview of the endoscopic system according to one or more embodiments of the present invention that illustrates a usage thereof.

The insertion part 11 is inserted into the guide catheter k01 beforehand (FIG. 20A). This has been done at the time of shipping out a product of the guide catheter k01 and the insertion part 11 or before an endoscopic examination.

Figure 20B:
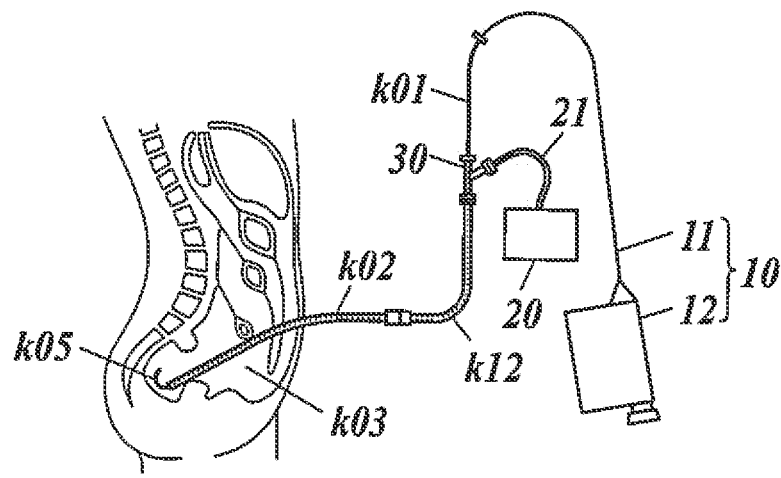
FIG. 20B is a schematic overview of the endoscopic system according to one or more embodiments of the present invention that illustrates a usage thereof.

First, the guide catheter k01 is inserted to the catheter k02 so that the distal extended part k05 is extended from the terminal opening k04 of the catheter k02 (FIG. 20B). During the insertion, fluid is fed from the fluid feeding means 20. The distal extended part k05 of the guide catheter k01 has such a flexibility that allows it to be stretched in a straight shape in the catheter k02 during the insertion but to return to the original shape with the curved front end when it comes out of the catheter k02.

Figure 20C:
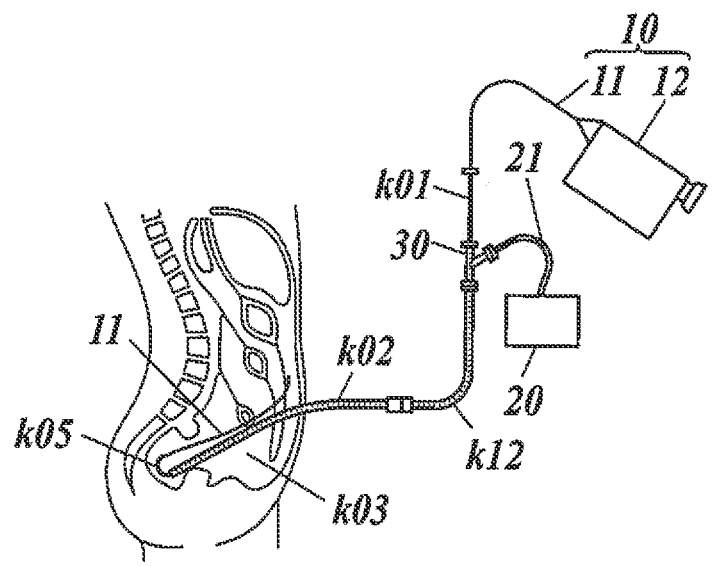
FIG. 20C is a schematic overview of the endoscopic system according to one or more embodiments of the present invention that illustrates a usage thereof.

Then, the insertion part 11 of the endoscope is pushed forward through the front end opening of the guide catheter k01 (FIG. 20C). During the insertion, fluid is similarly fed from the fluid feeding means 20. The front end of the insertion part 11 is guided from the distal opening of the guide catheter k01 in the predetermined direction k08. By further pushing the insertion part 11 forward with the guide in the predetermined direction k08, it is possible to bring the front end of the insertion part 11 to the upper part of the abdominal cavity k03 where there is an observation point. The front end of the insertion part 11 is placed and directed to the desired observation point, and an observation is made.

In both of the above-described Usage 1 and Usage 2 of one or more embodiments, the following operations can be made in order to change the endoscopic field. FIG. 21A, FIG. 21B, FIG. 21C, FIG. 21D and FIG. 21E are referenced for the description.

Figure 21A:
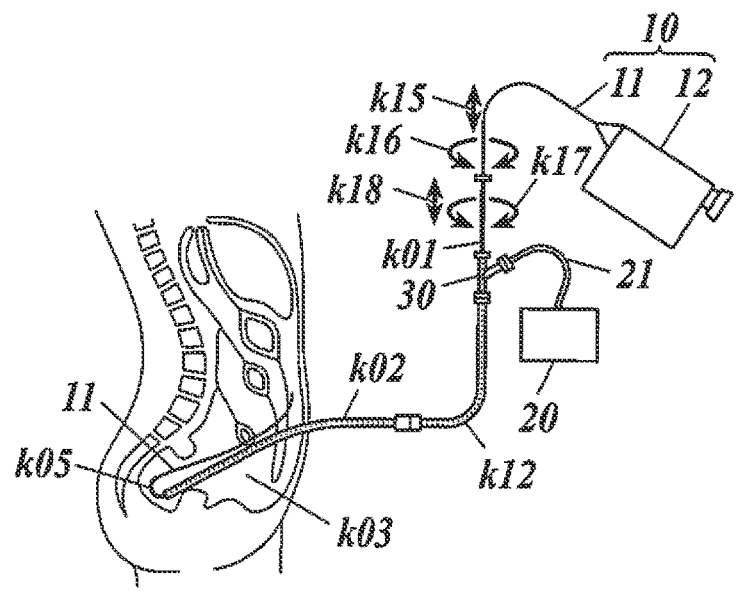
FIG. 21A is a schematic view of the endoscopic system according to one or more embodiments of the present invention that illustrates an operation for changing the endoscopic field.
Figure 21B:
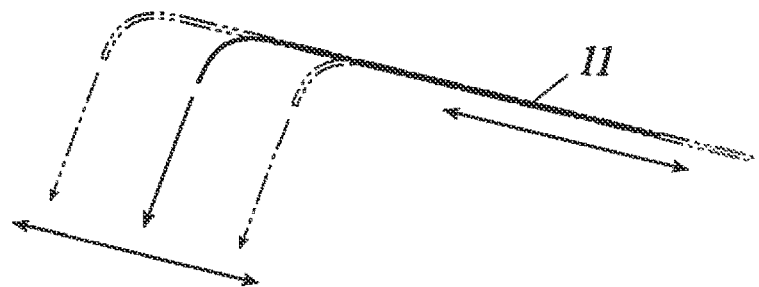
FIG. 21B is a schematic view of the endoscopic system according to one or more embodiments of the present invention that illustrates an operation for changing the endoscopic field.

By pushing and pulling the insertion part 11 as illustrated by the arrow k15 in FIG. 21A, it is possible to move up and down the front end of the insertion part 11 in the abdominal cavity k03 as illustrated in FIG. 21B, so that the endoscopic field can be moved.

Figure 21C:
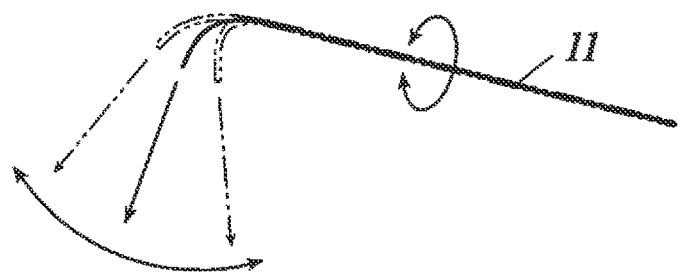
FIG. 21C is a schematic view of the endoscopic system according to one or more embodiments of the present invention that illustrates an operation for changing the endoscopic field.

By rotating the insertion part 11 about the axis as illustrated by the arrow k16 in FIG. 21A, it is possible to rotate the bent front end of the insertion part 11 as illustrated in FIG. 21C, so that the endoscopic field can be moved.

Figure 21D:
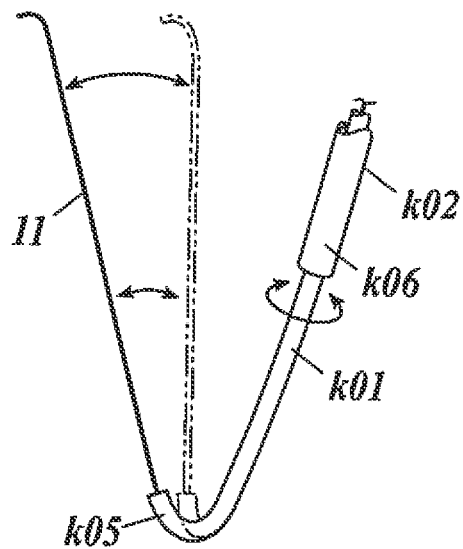
FIG. 21D is a schematic view of the endoscopic system according to one or more embodiments of the present invention that illustrates an operation for changing the endoscopic field.

By rotating the guide catheter k01 as illustrated by the arrow k17 in FIG. 21A, it is possible to rotate the part of the insertion part 11 extended from the guide catheter k01 about the axis of the terminal part k06 of the catheter k02 as illustrated in FIG. 21D, so that the endoscopic field can be moved.

Figure 21E:
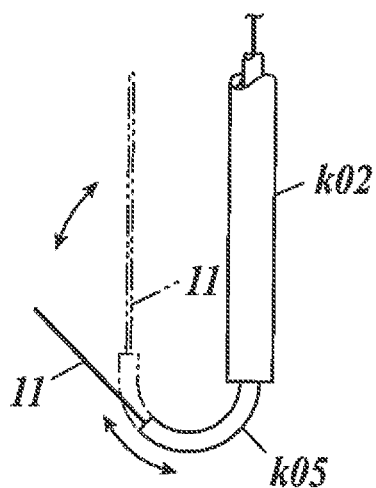
FIG. 21E is a schematic view of the endoscopic system according to one or more embodiments of the present invention that illustrates an operation for changing the endoscopic field.

Furthermore, by pushing and pulling the guide catheter k01 as illustrated by the arrow k18 in FIG. 21A, it is possible to adjust the extended length of the curved part of distal extended part k05 from the catheter k02 so as to change the initial angle of the part of the insertion part 11 extended from the guide catheter k01 as illustrated in FIG. 21E, so that the endoscopic field can be moved. Further, it is possible to move the endoscopic field similarly by means of the above-described bending mechanism that bends the distal extended part k05.

In this way, the front end of the insertion part 11 can be readily brought to an observation point. When the insertion part 11 is directly extended from the terminal opening k04 of the peritoneal dialysis catheter k02, the insertion part 11 bumps into the inner wall of the abdominal cavity near the Douglas' pouch, and an operation of changing the direction is therefore required. In contrast, with the guide catheter k01 whose front end is oriented in the upward direction of the body, it is possible to push the insertion part 11 smoothly to the upper part of the abdominal cavity k03. Therefore, it is possible to bring the front end of the insertion part 11 readily to an observation location.

Since the front end of the guide catheter k01 is oriented in the upward direction of the body, the front end of the insertion part 11 moves upward inside the abdominal cavity k03. Compared to extending the insertion part 11 directly from the terminal opening k04 of the peritoneal dialysis catheter k02, organs and the inner wall of the abdominal cavity are less likely to be hurt or damaged due to a contact with the insertion part 11.

The guide catheter k01 has a broader selection of materials and coating that are specialized for insertion of the endoscope than the peritoneal dialysis catheter k02. Accordingly, the slipperiness of the insertion part 11 in the guide catheter k01 can be improved, and the operability (ease of movement in the two axes of swing and forward/backward movement) of the insertion part 11 can therefore be improved. Furthermore, the additional operability of the guide catheter k01 expands the movable range of the front end of the insertion part 11, which improves the ease of operation and observation to a great extent.

Figure 22A:
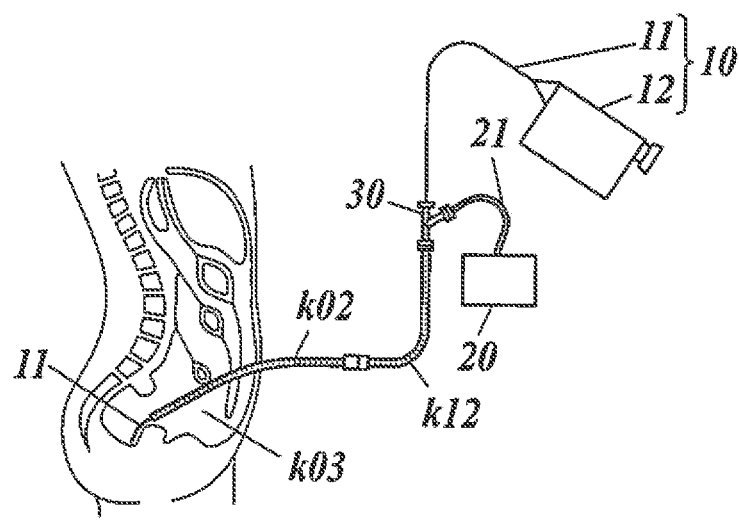
FIG. 22A is a schematic view that illustrates a trouble that occurs when the guide catheter is not used.
Figure 22B:
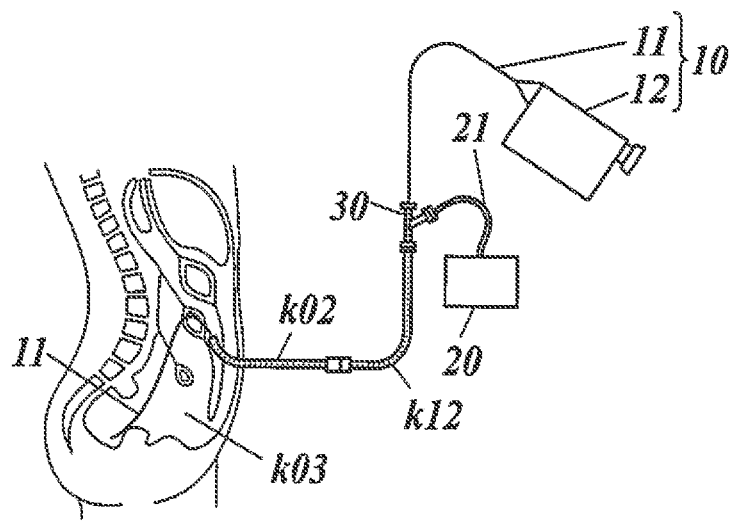
FIG. 22B is a schematic view that illustrates a trouble that occurs when the guide catheter is not used.
Figure 22C:
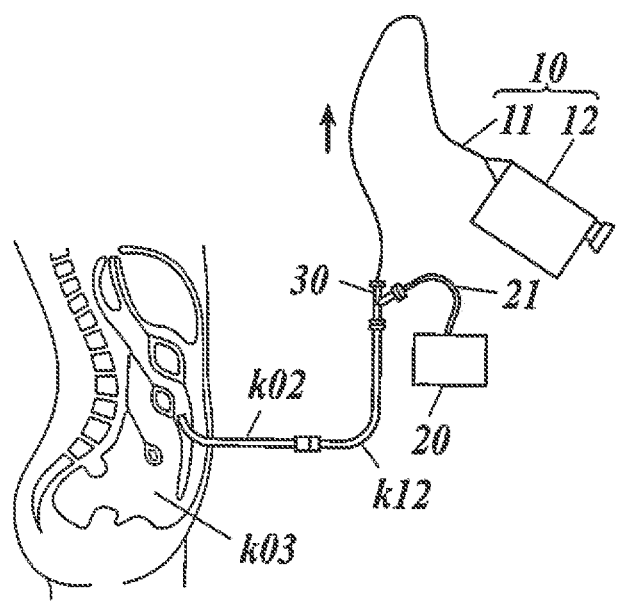
FIG. 22C is a schematic view that illustrates a trouble that occurs when the guide catheter is not used.

When the insertion part 11 is directly extended from the terminal opening k04 of the peritoneal dialysis catheter k02 as illustrated in FIG. 22A, FIG. 22B and FIG. 22C, the front end of the insertion part 11 sometimes pushes the inner wall of the abdominal cavity (near the Douglas' pouch) downward (FIG. 22B), and the whole catheter k02 is thereby curved and displaced from the right position.

The retained position of the front end of the catheter k02 is displaced from the vicinity of the Douglas' pouch. Even after removing the insertion part 11, the peritoneal dialysis catheter k02 remains deviated (FIG. 22C), which results in a failure in a subsequent exchange of the dialysate for peritoneal dialysis.

However, when the guide catheter k01 is used according to the above-described usages, the front end of the insertion part 11 does not push the inner wall of the abdominal cavity downward. Therefore, the peritoneal dialysis catheter k02 is less likely to be displaced from the right position.

Figure 23A:
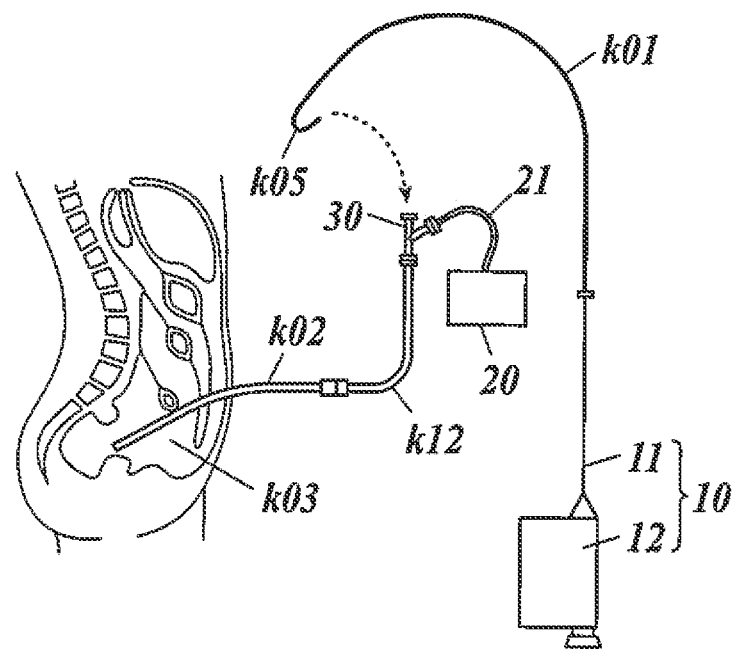
FIG. 23A is a schematic view that illustrates a trouble that occurs when a curved part of the guide catheter is too rigid.
Figure 23B:
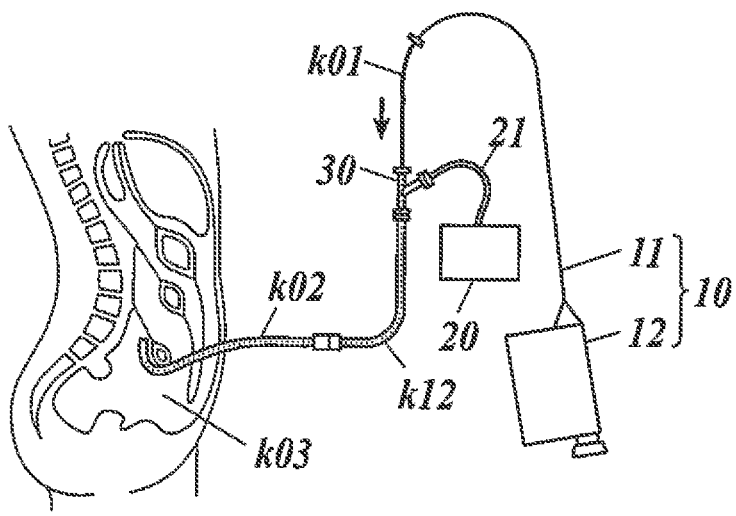
FIG. 23B is a schematic view that illustrates the trouble that occurs when the curved part of the guide catheter is too rigid.

When the guide catheter k01 that has the distal extended part k05 originally formed in a curved shape is inserted in the peritoneal dialysis catheter k02 as illustrated in FIG. 23A, the peritoneal dialysis catheter k02 may be displaced from the right position as illustrated in FIG. 23B depending on the rigidness of the curved part of the guide catheter k01.

To avoid this, it is required that the distal extended part k05 is sufficiently bendable. For this reason, the curved part of the distal extended part k05 is formed more flexible than the other part (straight part) of the guide catheter k01.

Figure 24A:
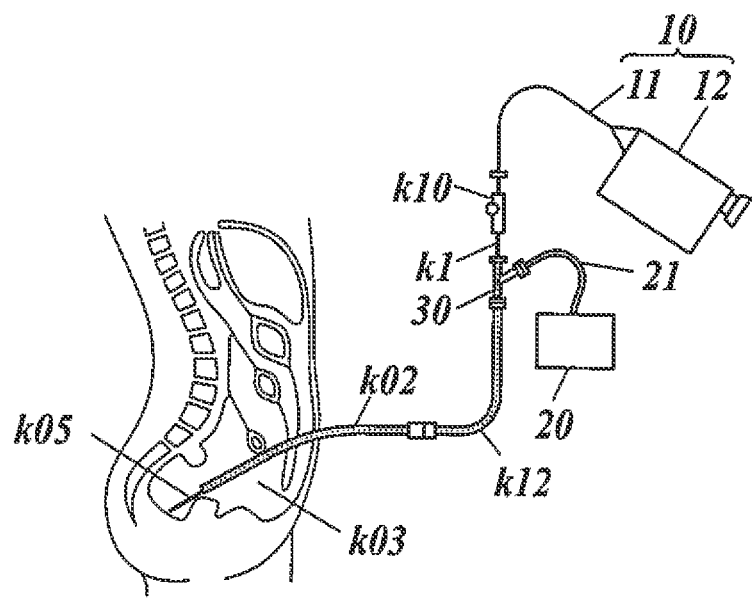
FIG. 24A is a schematic overview of the endoscopic system according to one or more embodiments of the present invention that illustrates a usage thereof that involves a bending operation of the guide catheter.
Figure 24B:
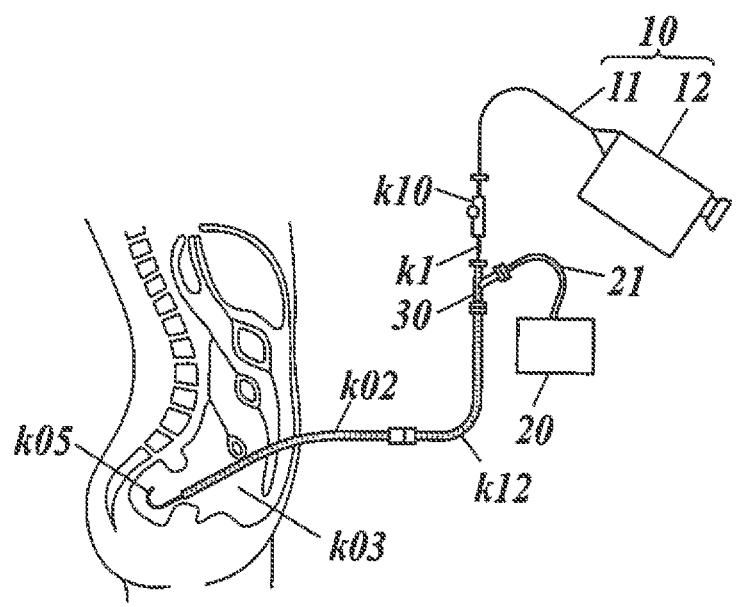
FIG. 24B is a schematic overview of the endoscopic system according to one or more embodiments of the present invention that illustrates the usage thereof that involves a bending operation of the guide catheter.

Alternatively, a bending mechanism for bending the distal extended part k05 is provided, and the distal extended part k05 is kept in a straight shape as illustrated in FIG. 24A during the insertion. This can reduce the chance of a deviation of the peritoneal dialysis catheter k02 from the right position. After the insertion of the guide catheter k01, the distal extended part k05 is bent as illustrated in FIG. 24B, and the insertion part 11 is pushed forward according to the above-described usages.

Configuration 4

Next, a configuration of the fluid feeding structure of one or more embodiments will be described as Configuration 4.

In the above-described Configuration 2 and Configuration 3, fluid is fed from the fluid feeding means 20 into the peritoneal dialysis catheter k02 through the joint 30 in order to improve the lubricity between the guide catheter k01 and the peritoneal dialysis catheter k02. In order to further improve the lubricity, it is effective to provide hydrophilic coating on the outer surface of the guide catheter k01. It is also effective to provide hydrophilic coating on the inner surface of the extension catheter k12.

Figure 25A:
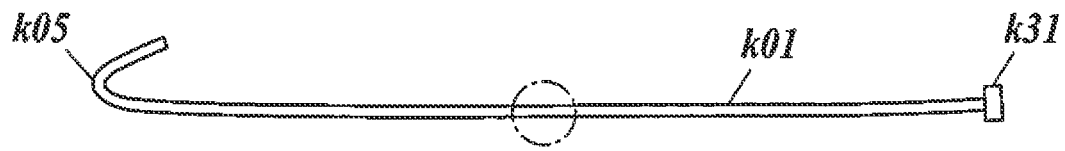
FIG. 25A is a schematic view of one or more embodiments of the present invention that illustrates a configuration in which the guide catheter has side holes.
Figure 25B:
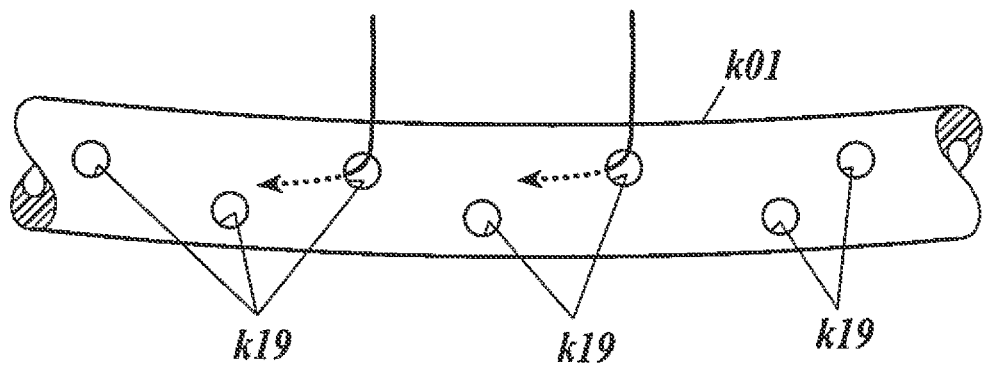
FIG. 25B is a schematic view of the side portion of the guide catheter in FIG. 25A that illustrates the details thereof.

In an additional configuration, the guide catheter k01 may have side holes k19 for communicating fluid as illustrated in FIG. 25A and FIG. 25B.

The side holes k19 are formed in the side wall of the guide catheter k01. It is required that the side holes k19 are located in the part closer to the base end than the distal extended part k05. Further, the part having the side holes k19 are located inside the joint 30 when the distal extended part k05 is extended from the terminal opening k04 of the peritoneal dialysis catheter k02.

The fluid fed from the fluid feeding means 20 into the joint 30 can flow into the guide catheter k01 through the side holes k19.

As a result, the lubricity between the guide catheter k01 and the insertion part 11 is improved. In order to further improve the lubricity, it is effective to provide hydrophilic coating on the inner surface of the guide catheter k01. It is also effective to provide hydrophilic coating on the outer surface of the insertion part 11.

Other Configurations

Next, another configuration of one or more embodiments will be described in which the fluid feeding means 20 and the joint 30 are integrated with each other.

Figure 26A:
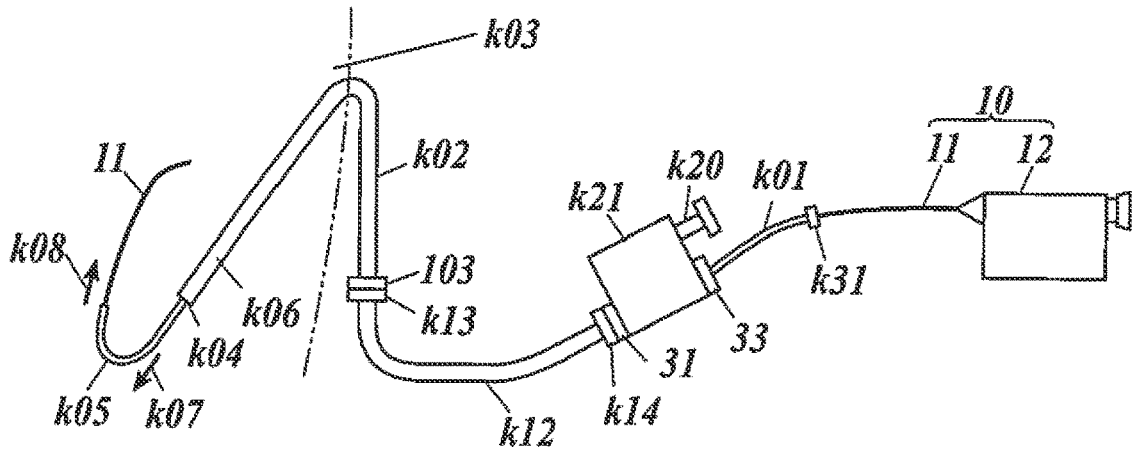
FIG. 26A is a schematic view of one or more embodiments of the present invention that illustrates a configuration in which a fluid feeding means is integrated with a joint.

As illustrated in FIG. 26A, a syringe k20 as the fluid feeding means 20 can be integrated with the joint 30 to constitute a unit k21.

Figure 26B:
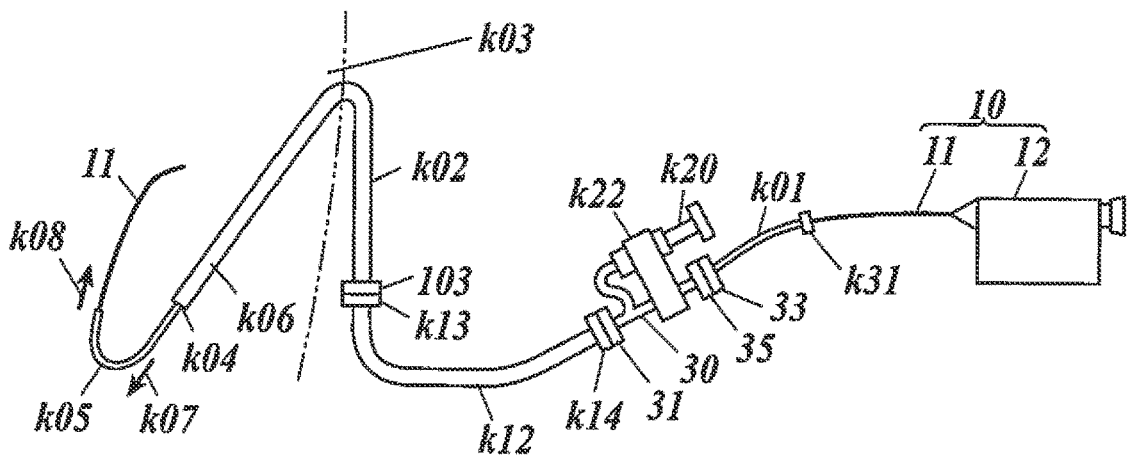
FIG. 26B is a schematic view of one or more embodiments of the present invention that illustrates a configuration in which a fluid feeding means is integrated with a joint.

Alternatively, as illustrated in FIG. 26B, a unit k22 may be used which integrally holds a cylinder of the syringe k20 and a tube part of the joint 30.

Figure 26C:
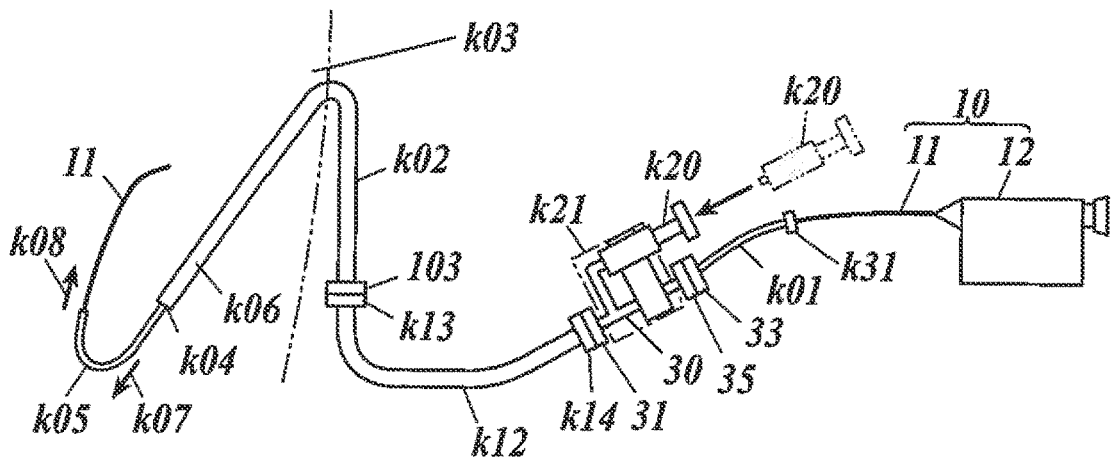
FIG. 26C is a schematic view of one or more embodiments of the present invention that illustrates a configuration in which a fluid feeding means is integrated with a joint.

Alternatively, as illustrated in FIG. 26C, the syringe k20 may be detachably attached to the unit k21.

The integrated fluid feeding means 20 is not limited to a syringe.

As described above, the operability can be improved by integrating the fluid feeding means 20 with the joint 30. For example, the holdability can be improved. Further, an operator who holds the fluid feeding means 20 and an operator who holds the joint 30 can be the same person, and the number of operators can thus be reduced.

Figure 27A:
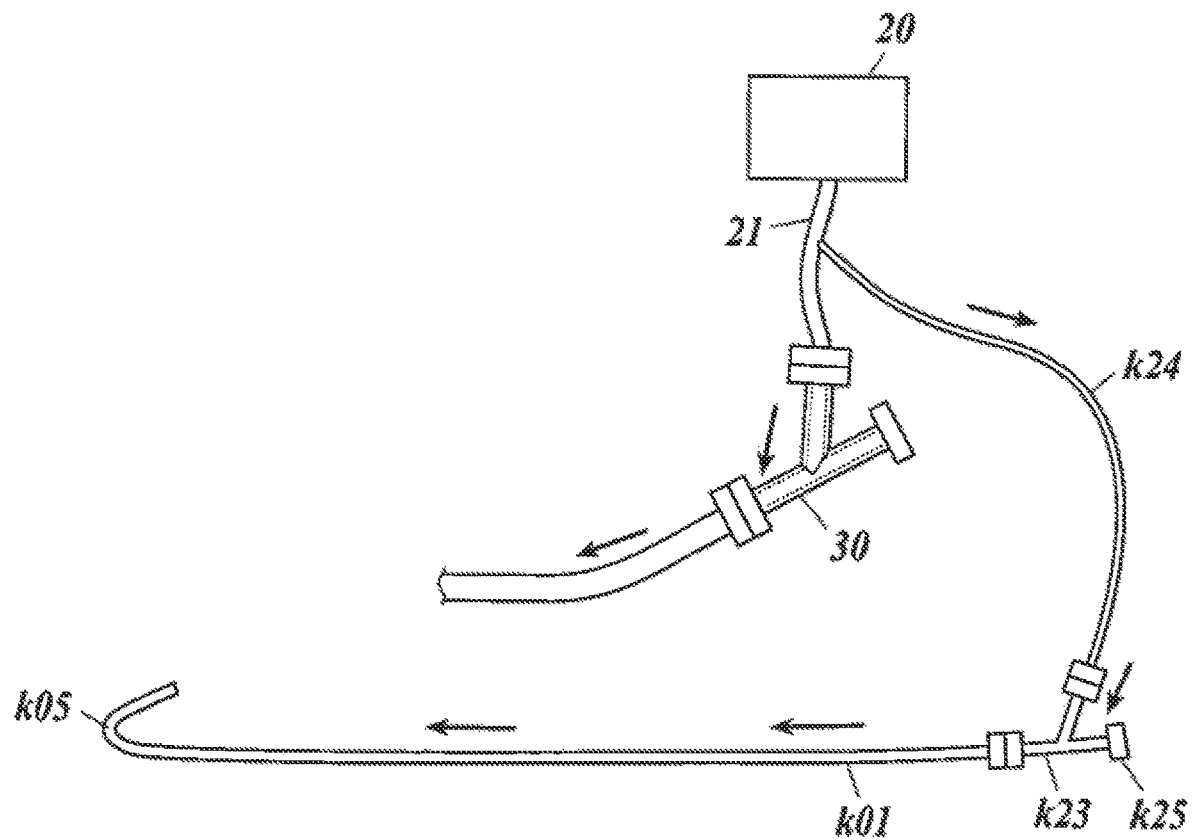
FIG. 27A is a schematic view of one or more embodiments of the present invention that illustrates a configuration that includes a structure of directly feeding fluid individually to the peritoneal dialysis catheter and to the guide catheter.
Figure 27B:
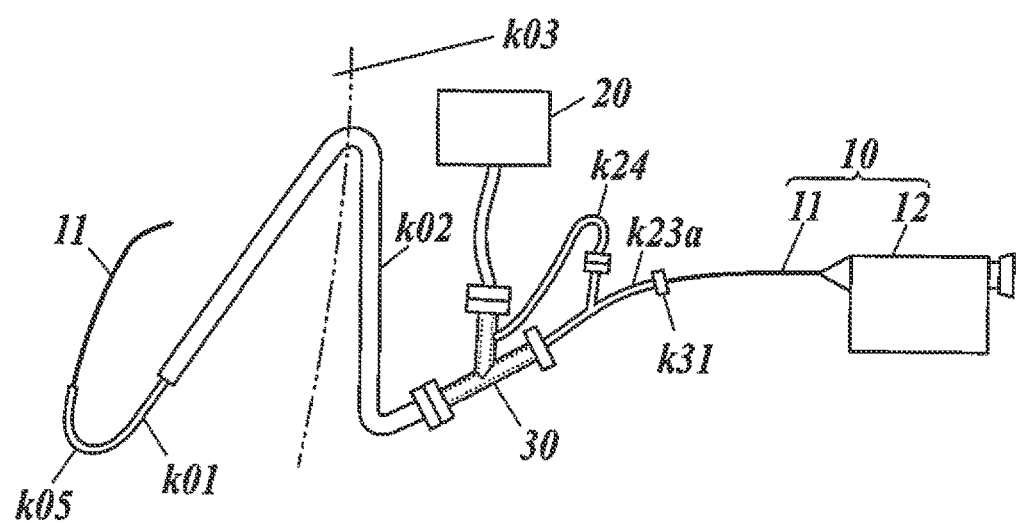
FIG. 27B is a schematic view of one or more embodiments of the present invention that illustrates a configuration that includes the structure of directly feeding fluid individually to the peritoneal dialysis catheter and to the guide catheter.

Next, another configuration will be described which includes the fluid feeding structure as illustrated in FIG. 27A and FIG. 27B instead of the above-described side holes k19.

As illustrated in FIG. 27A, a trifurcate joint k23 similar to the joint 30 is connected to the base end of the guide catheter k01, and a branch channel k24 from the fluid feeding means 20 is connected to the joint k23. The trifurcate joint k23 also has an insertion opening k25 for inserting the insertion part 11 to the joint k23.

The branch channel k24 may be either branched from the infusion tube 21 as illustrated in FIG. 27A or branched from the joint 30 as illustrated in FIG. 27B.

As illustrated in FIG. 27B, the joint k23 may be integrated with the base end of the guide catheter k01. That is, the guide catheter k01 may have a bifurcate structure k23a at the base end.

Figure 28A:
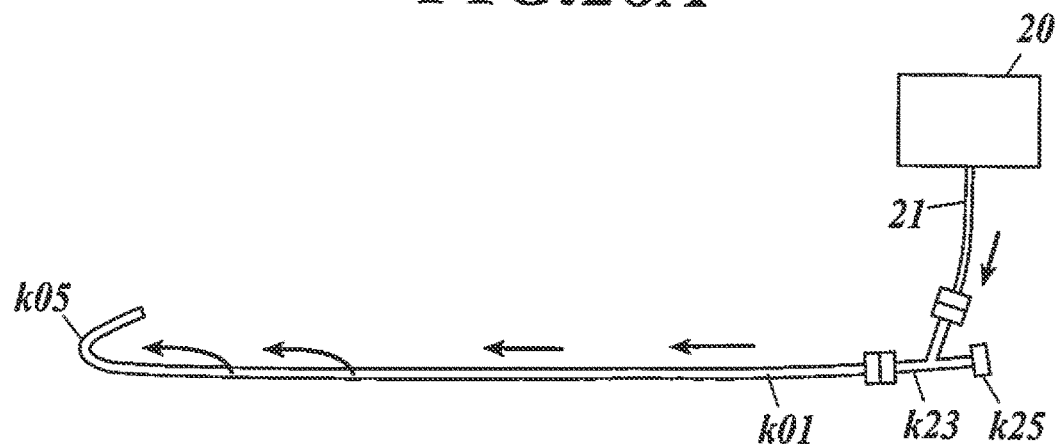
FIG. 28A is a schematic view of one or more embodiments of the present invention that illustrates a configuration that includes the structure of directly feeding fluid only to the guide catheter.
Figure 28B:
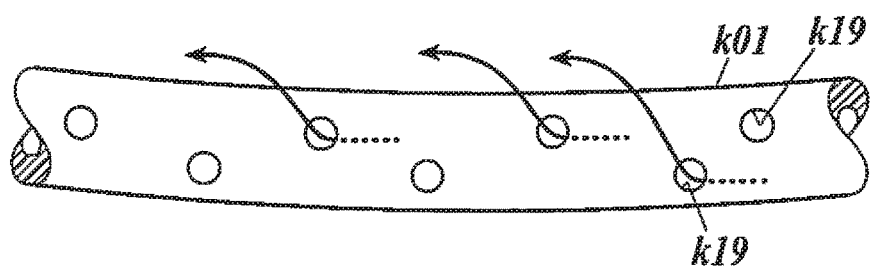
FIG. 28B is a schematic view of one or more embodiments of the present invention that illustrates a configuration that includes the structure of directly feeding fluid only to the guide catheter.
Figure 28C:
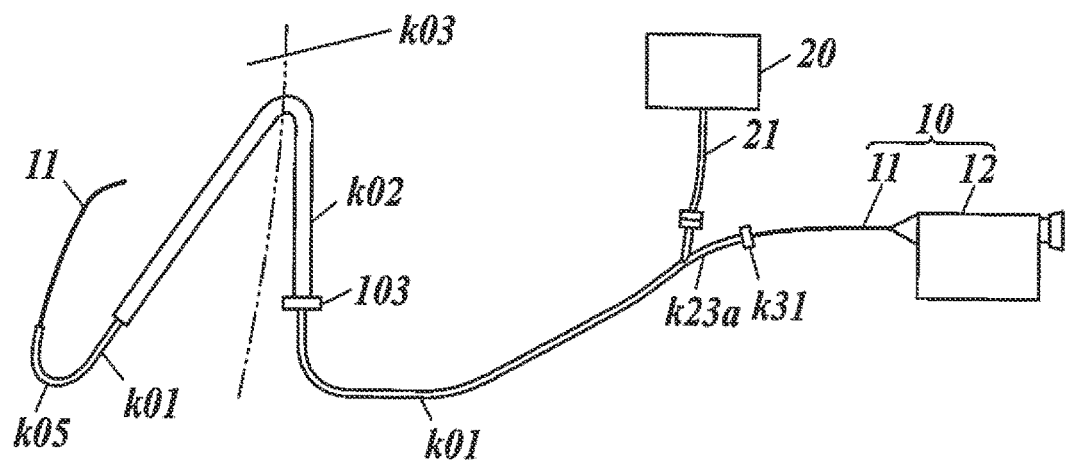
FIG. 28C is a schematic view of one or more embodiments of the present invention that includes the structure of directly feeding fluid only to the guide catheter.

Next, another configuration of the fluid feeding structure will be described which has the above-described side holes k19 while it does not include the joint 30 but includes the joint k23 as illustrated in FIG. 28A, FIG. 28B and FIG. 28C.

As illustrated in FIG. 28A, fluid is fed from the fluid feeding means 20 into the guide catheter k01 though the joint k23. As illustrated in FIG. 28B, the guide catheter k01 has the side holes k19, and the fluid can be fed also into the peritoneal dialysis catheter k02 in the fluid feeding structure as illustrated in FIG. 28C. This can facilitate the insertion of the insertion part 11 and the guide catheter k01.

Figure 29:
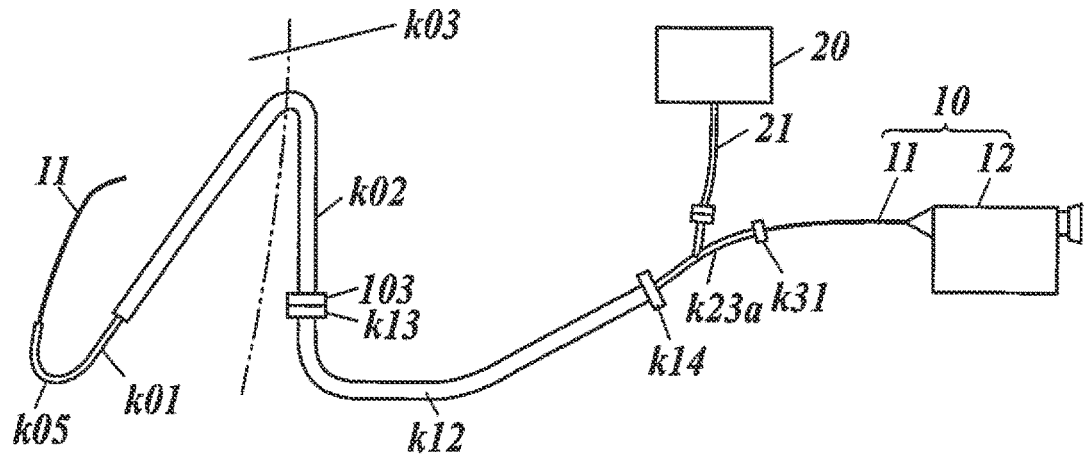
FIG. 29 is a schematic view of one or more embodiments of the present invention that illustrates a configuration that includes a structure of directly feeding fluid only to the guide catheter and also includes an extension catheter.

In this configuration, the extension catheter k12 is connected, and a backflow prevention mechanism is provided in the connector k14 of the extension catheter k12 as illustrated in FIG. 29. This is effective when there is no backflow prevention mechanism in the proximal end 103 of the peritoneal dialysis catheter k02 or when it is impossible to provide a backflow prevention mechanism in the proximal end 103.

Next, configurations of marks of one or more embodiments provided in the guide catheter k01 will be described.

Figure 30A:
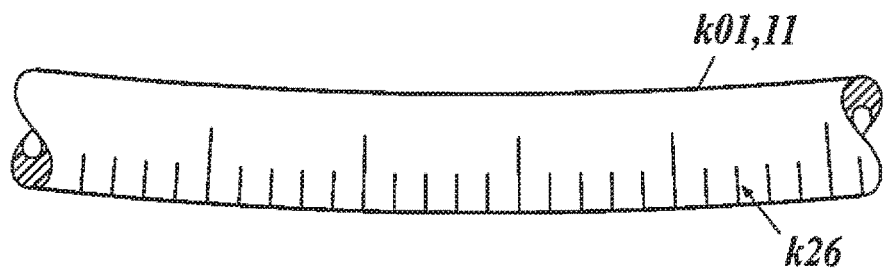
FIG. 30A is a schematic view of one or more embodiments of the present invention that illustrates a configuration of the guide catheter and a mark provided on the insertion part of the endoscope.

As illustrated in FIG. 30A, a scale mark k26 is provided in the guide catheter k01 to indicate the inserted length.

Figure 30B:
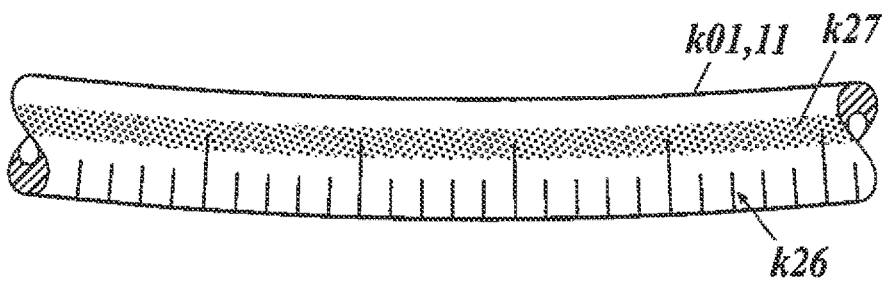
FIG. 30B is a schematic view of one or more embodiments of the present invention that illustrates a configuration of the guide catheter and a mark provided on the insertion part of the endoscope.

Further, as illustrated in FIG. 30B, a mark k27 is provided in the guide catheter k01 to indicate the orientation of the curvature of the distal extended part k05. The mark k27 is provided extending in the axial direction of the guide catheter k01, for example, at a circumferential position corresponding to the inner side of the curvature of the distal extended part k05.

Figure 30C:
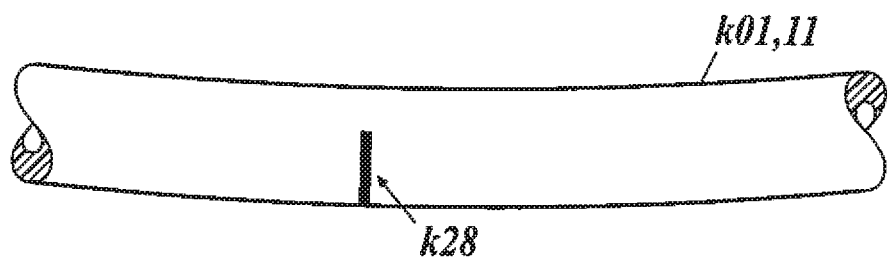
FIG. 30C is a schematic view of one or more embodiments of the present invention that illustrates a configuration of the guide catheter and a mark provided on the insertion part of the endoscope.
Figure 30D:
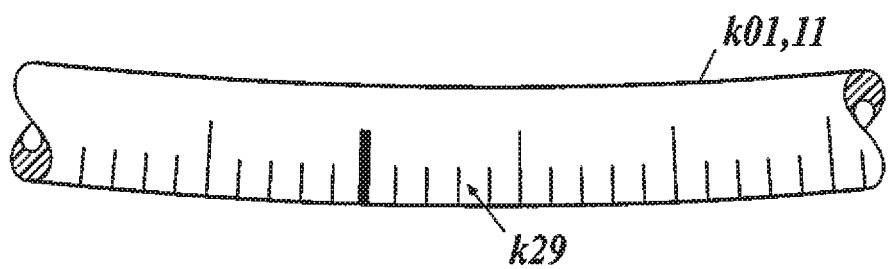
FIG. 30D is a schematic view of one or more embodiments of the present invention that illustrates a configuration of the guide catheter and a mark provided on the insertion part of the endoscope.

As a mark indicating the inserted length of the guide catheter k01, for example, a mark k28 may be provided to indicate a reference position in the axial direction as illustrated in FIG. 30C. The scale mark k26 and the mark k28 indicating the reference position may be combined into a mark 29k (FIG. 30D).

Figure 30E:
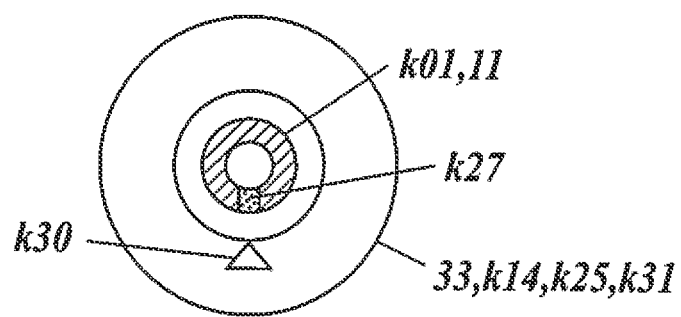
FIG. 30E is a schematic view of one or more embodiments of the present invention that illustrates a configuration of the guide catheter and a mark provided on the insertion part of the endoscope.

To enable setting the orientation of the curvature of the distal extended part k05 into a predetermined direction, a mark k30 is provided at the insertion opening 33 of the joint 30 with which the mark k27 is aligned as illustrated in FIG. 30E. In the configuration of FIG. 29, since the joint 30 is not used, the mark 30 is provided at the connector k14 of the extension catheter k12 that serves as the insertion opening.

To adjust the extension of the distal extended part k05 to a predetermined length, the mark k28 indicating the reference position in the axial direction is aligned with the end face of the insertion opening 33 of the joint 30. Similarly, in the configuration of FIG. 29, since the joint 30 is not used, the mark k28 is configured to be aligned with the end face of the connector k14 of the extension catheter k12 that serves as the insertion opening. When the extension catheter k12 is not used, the marker k28 may be configured be aligned with the proximal end 103 of the peritoneal dialysis catheter k02.

By using these marks, it is possible to understand and control the inserted length of the guide catheter k01, i.e. the extended length of the distal extended part k05. Further, it is also possible to understand and control the direction in which the distal extended part k05 comes out and curves from the terminal opening k04 of the peritoneal dialysis catheter k02.

The extension catheter k12 and the guide catheter k01, including the above-described marks, are configured according to the type of the peritoneal dialysis catheter k02. However, a scale mark can be generally used regardless of the type of the peritoneal dialysis catheter k02.

The insertion part 11 is also provided with marks similar to those provided in the guide catheter k01. In this case, the guide catheter k01 and the insertion opening 33 of the joint 30 in FIG. 30A to FIG. 30E correspond respectively to the insertion part 11 and the insertion opening k31 (or possibly the insertion opening k25) of the guide catheter k01.

Accordingly, it is possible to check how long the front end of the insertion part 11 is extended from the front end of the guide catheter k01 during the insertion of the insertion part 11. Further, it is also possible to check the orientation of the bent front end of the insertion part 11. With regard to the marks provided in the insertion part 11, a mark k28 indicating the reference position in the axial direction is not affected by the length of the peritoneal dialysis catheter k02 since the reference position is determined according to the relationship between the length of the insertion part 11 and the length of the guide catheter k01.

The angle around the axis of the guide catheter k01 can be checked by a method of an operator visually checking the mark k27 in hand or by a method of checking an endoscopic image. To carry out the former method, the mark k27 is provided at least in a manner recognizable from the outside. To carry out the latter method, the mark k27 is provided at least in a manner that can be imaged by the endoscope from the inside. For these purposes, the mark is provided in the outer surface and/or the inner surface of the tube of the guide catheter k01, or a transparent material of the tube is combined with the mark material so that the mark is visible through the outer surface and/or the inner surface.

The marks are made of a material detectable by means of X-ray or ultrasound. This enables recognizing the marks from outside by taking an X-ray photographic image or an ultrasonic photographic image, which improves the workability.

The curved part of the guide catheter k01 can be stretched by inserting the curved part of the insertion part 11 into the curved part of the guide catheter k01 in such a manner that they curve in a mutually opposite orientation. In this way, it is possible to improve the ease of the insertion to the peritoneal dialysis catheter k02. Such insertion can be performed by using the above-described marks.

INDUSTRIAL APPLICABILITY

The present invention is applicable to constituting a useful endoscope.

REFERENCE SIGNS LIST

1 Endoscopic system
10 Endoscope
11 Insertion part
12 Operational part
20 Fluid feeding means
21 Infusion tube
22 Output end
30 Joint
31 First connector part
32 Second connector part
33 Insertion opening
34 Communication channel
34a Confluence part
35 Check valve
40 Conversion connector
41 Third connector part
42 Fourth connector part
100 Indwelling catheter
101 Bent part
102 Spiral part
103 Proximal end
104 Distal end (The following reference signs are only for FIG. 11 to FIG. 15B.)

k01 Marker
k02 Peritoneal dialysis catheter
k03 Abdominal cavity
k04 Distal extended part
k05 Straight part
k06 First curved part
k07 Straight part
k08 Second curved part
k11 Straight part
k12 First curved part
k13 Straight part
k14 Second curved part (The following reference signs are only for FIG. 16 to FIG. 30E.)

k01 Guide catheter
k02 Peritoneal dialysis catheter

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. An endoscopic system, comprising:
a flexible insertion part comprising:
an imaging optical system comprising a lens or an image fiber; and
a light source that is covered with an exterior tube;
an operational part connected to a base end of the insertion part; and
a guide catheter, in which the insertion part is inserted, that guides the insertion part,
wherein the guide catheter:
is inserted through an indwelling catheter that guides the guide catheter within a body cavity; and
guides the insertion part in a direction different from an extending direction of the indwelling catheter when the guide catheter is extended from a terminal opening of the indwelling catheter,
wherein the insertion part is guided by a curvature of a distal extended part of the guide catheter,
wherein the curvature of the distal extended part of the guide catheter:
includes grooves disposed on an outer surface of the guide catheter; and bends, at the grooves, during an operation of the guide catheter using a wire that is coupled to the guide catheter and an operation dial and is operated via the operation dial, wherein the endoscopic system further comprises:
(a) a fluid feeding means comprising an infusion bag and an infusion pump, or comprising a syringe and a syringe pump; and
(b) a joint that comprises:
a first connector part that is connected to a proximal end of the indwelling catheter;
a second connector part connected to an output end of the fluid feeding means;
an insertion opening in which the guide catheter is inserted; and
a channel that communicates the first connector part to the second connector part at one end and the insertion opening at another end through a confluent part, and wherein the guide catheter has a side hole through which a fluid fed from the fluid feeding means to the joint flows into the guide catheter.

2. The endoscopic system according to claim 1, wherein a front end of the insertion part has an originally formed curved shape or comprises a bending mechanism which is operated during use for bending the front end.

3. The endoscopic system according to claim 1, wherein the guide catheter enters the joint from the insertion opening to the channel, and can pass through the confluent part and the first connector part to enter the indwelling catheter connected to the first connector part, and wherein fluid fed from the fluid feeding means that is connected to the second connector part passes through the confluent part and the first connector part to flow into the indwelling catheter connected to the first connector part.

4. The endoscopic system according to claim 3, wherein the joint comprises a check valve between the insertion opening and the confluent part to prevent the fluid from leaking through the insertion opening.

5. The endoscopic system according to claim 3, wherein the guide catheter comprises a hydrophilic coating on an outer face of the guide catheter.

6. The endoscopic system according to claim 3, wherein the guide catheter comprises a hydrophilic coating on an inner face of the guide catheter.

7. The endoscopic system according to claim 3, wherein the joint comprises a valve that fixes the guide catheter to the joint, the guide catheter is inserted through the insertion opening.

8. The endoscopic system according to claim 1, wherein a mark that indicates an orientation of the curvature is provided in the guide catheter.

9. The endoscopic system according to claim 1, wherein a mark that indicates an inserted length is provided in the guide catheter.

10. The endoscopic system according to claim 1, wherein a mark that indicates an insertion length is provided in the insertion part.

11. The endoscopic system according to claim 1, wherein the exterior tube comprises a hydrophilic coating on an outer face of the exterior tube.

* * * * *